(12) United States Patent
Jung et al.

(10) Patent No.: US 11,685,702 B2
(45) Date of Patent: Jun. 27, 2023

(54) METHOD FOR PRODUCING ARENE COMPOUNDS AND ARENE COMPOUNDS PRODUCED BY THE SAME

(71) Applicant: JSI Silicone Co., Seongnam-si (KR)

(72) Inventors: Il Nam Jung, Yongin-si (KR); A Ra Cho, Seongnam-si (KR); Seung Hwan Kang, Seoul (KR); Young Min Kim, Seongnam-si (KR)

(73) Assignee: JSI SILICONE CO., Seongnam-si (KR)

( * ) Notice: Subject to any disclaimer, the term of this patent is extended or adjusted under 35 U.S.C. 154(b) by 30 days.

(21) Appl. No.: 17/113,695

(22) Filed: Dec. 7, 2020

(65) Prior Publication Data

US 2021/0188739 A1 Jun. 24, 2021

(30) Foreign Application Priority Data

Dec. 20, 2019 (KR) .................. 10-2019-0171734
Feb. 7, 2020 (KR) .................. 10-2020-0015255
Aug. 18, 2020 (KR) .................. 10-2020-0103421

(51) Int. Cl.
| | | |
|---|---|---|
| C07C 2/86 | (2006.01) | |
| C07C 17/266 | (2006.01) | |
| C07C 15/50 | (2006.01) | |
| C07C 15/58 | (2006.01) | |
| C07C 25/24 | (2006.01) | |
| C07C 15/60 | (2006.01) | |
| C07C 45/69 | (2006.01) | |
| C07C 49/796 | (2006.01) | |
| C07C 15/62 | (2006.01) | |
| C07C 43/285 | (2006.01) | |
| C07C 41/30 | (2006.01) | |
| C07C 15/24 | (2006.01) | |
| C07C 15/16 | (2006.01) | |
| C07C 15/20 | (2006.01) | |
| C07F 7/18 | (2006.01) | |
| C07C 319/20 | (2006.01) | |
| C07C 321/28 | (2006.01) | |
| C07F 7/12 | (2006.01) | |
| C07C 15/44 | (2006.01) | |

(52) U.S. Cl.
CPC ............ *C07C 2/861* (2013.01); *C07C 15/16* (2013.01); *C07C 15/20* (2013.01); *C07C 15/24* (2013.01); *C07C 15/44* (2013.01); *C07C 15/50* (2013.01); *C07C 15/58* (2013.01); *C07C 15/60* (2013.01); *C07C 15/62* (2013.01); *C07C 17/266* (2013.01); *C07C 25/24* (2013.01); *C07C 41/30* (2013.01); *C07C 43/285* (2013.01); *C07C 45/69* (2013.01); *C07C 49/796* (2013.01); *C07C 319/20* (2013.01); *C07C 321/28* (2013.01); *C07F 7/12* (2013.01); *C07F 7/127* (2013.01); *C07F 7/1804* (2013.01); *C07F 7/1892* (2013.01); *C07C 2603/24* (2017.05); *C07C 2603/50* (2017.05); *C07C 2603/52* (2017.05)

(58) Field of Classification Search
CPC ......... C07C 2/861; C07C 15/02; C07C 15/12; C07C 15/14; C07C 15/16; C07C 15/20; C07C 15/24; C07C 15/44; C07C 15/50; C07C 15/58; C07C 15/60; C07C 15/62; C07C 15/27; C07C 15/56; C07C 17/266; C07C 17/32; C07C 25/22; C07C 25/24; C07C 41/30; C07C 43/205; C07C 43/285; C07C 45/68; C07C 45/69; C07C 49/683; C07C 49/796; C07C 319/20; C07C 321/28; C07C 321/30; C07C 2603/24; C07C 2603/46; C07C 2603/50; C07C 2603/52; C07C 2527/228; C07F 7/12; C07F 7/127; C07F 7/1804; C07F 7/1892; C07F 9/5407
See application file for complete search history.

(56) References Cited

U.S. PATENT DOCUMENTS

2004/0236057 A1* 11/2004 Chevalier .............. C08G 77/06
528/42

OTHER PUBLICATIONS

Kodomari et al. ("Direct Allylation of Aromatic Compounds with Allylic Chloride using the Supported Reagents Systems ZnCl2/SiO2-K2CO3/Al2O3." J. Chem. Soc., Chem. Commun., 18 (1995): 1895-1896) (Year: 1995).*

(Continued)

*Primary Examiner* — In Suk C Bullock
*Assistant Examiner* — Jason Y Chong
(74) *Attorney, Agent, or Firm* — Cantor Colburn LLP

(57) ABSTRACT

Provided is a method for producing (alkyl)arene compounds represented by Formulae 3-1, 3-2, and 3-3 by the Friedel-Crafts alkylation reaction of alkyl halide compounds and arene compounds using organic phosphine compounds as a catalyst.

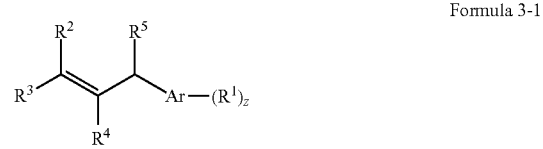

Formula 3-1

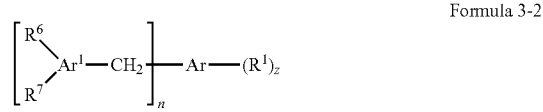

Formula 3-2

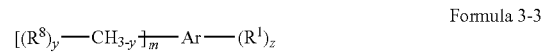

Formula 3-3

12 Claims, No Drawings

(56) References Cited

OTHER PUBLICATIONS

Ichihara ("Functional selectivity in Friedel-Crafts alkylations with allylic halides promoted by solid composite lead fluoride reagent." Chem. Commun., 19 (1997): 1921-1922) (Year: 1997).*

Cho, et al., Novel Phosphonium Chloride-Catalyzed Dehydrohalogenative Si-C Coupling Reaction of Alkyl Halides with Trichlorosilane, J. Am. Chem. Soc., 2001, vol. 123, pp. 5584-5585.

Roberts, et al., Friedel-Crafts Alkylation Chemistry, Marcel Dekker, Inc., New York, New York, USA, 1984.

Selvaraj, et al., Room temperature synthesis of diphenylmethane over novel mesoporous Lewis acid catalysts, Journal of Molecular Catalysis A: Chemical, 2006, vol. 243, pp. 176-182.

* cited by examiner

METHOD FOR PRODUCING ARENE COMPOUNDS AND ARENE COMPOUNDS PRODUCED BY THE SAME

BACKGROUND OF THE INVENTION

1. Field of the Invention

The present invention relates to alkyl arene compounds and a method for producing the same, and more particularly, to alkyl arene compounds synthesized by the Friedel-Crafts alkylation reaction using an organic phosphine catalyst, and a method for producing the same.

2. Description of the Related Art

The Friedel-Crafts alkylation reaction is a very important reaction for the synthesis of alkyl substituted arene compounds, and has been widely used for more than a century (Roberts, Royston M; Khalaf, Ah, *Friedel-Crafts Alkylation Chemistry*, Marcel Dekker, Inc., New York, N.Y., USA, 1984). It is known that the Friedel-Crafts reaction always requires a Lewis acid catalyst, such as aluminum chloride, boron chloride and iron chloride. In the Friedel-Crafts alkylation reaction, Lewis acids of metal halides attract a halide of an alkyl halide compound to give alkyl cations while the metal tetrahalide anions are formed, followed by the electrophilic substitution reaction of alkyl cations to the arenes having high electron density occurs. The Lewis acid catalysts easily form a coordination bond with arene compounds having more benzene rings than the anthracene and the activity of the catalyst would be greatly deteriorated, so that the Lewis acid catalyst is neither practical nor easy to remove the complex from the reaction mixture after the reaction. Therefore, it has been reported that when diphenylmethane is synthesized by the Friedel-Crafts alkylation reaction of benzene with benzyl chloride, the inorganic solid of acidic silica is used as a catalyst, and then the catalyst can be easily removed after the reaction (Selvaraj, M.; Lee, T. G. *Journal of Molecular Catalysis A: Chemical* 2006, 243(2), 176-182). Accordingly, in order to introduce an organic substituent to the anthracene or arene compounds having higher number of benzene rings than anthracene, a neutral or basic catalyst is required instead of an acid catalyst. However, little is known about neutral catalysts suitable for the Friedel-Crafts alkylation reaction.

Meanwhile, it has been known that in the reaction of alkyl halides with trichlorosilane in the presence of organic phosphonium chloride as a catalyst, hydrogen halide is generated by taking hydrogen from trichlorosilane and halogen from alkyl halides to give alkylchlorosilane, which is called the dehydrohalogenative Si—C coupling reaction (Yeon Seok Cho, Y. S.; Kang, S.-H.; Han, J. S.; Yoo, B. R.; Jung, I. N., *J. Am. Chem. Soc.* 2001, 123, 5584). As disclosed in the above prior art, tertiary organic phosphine or organic phosphonium chloride is used as a catalyst in the dehydrohalogenative Si—C coupling reaction. The organic phosphonium chloride is neutral and a tertiary organic phosphine is basic rather than acidic. The tertiary organic phosphine reacts with alkyl halide to form a quaternary organic phosphonium halide. This dehydrohalogenative Si—C coupling reaction occurs at around 150° C. and the reaction of highly active benzyl chloride occurs at slightly lower temperature, but in the case of unactive alkyl chlorides the reaction does not occur until the reaction temperature reaches to approximately 170° C. However, this reaction is an exothermic reaction, and the reaction temperature easily goes up around 200° C. When toluene was used as a solvent in the reaction of benzyl chloride with trichlorosilane, benzyltoluene was obtained as a byproduct in addition to benzyl trichlorosilane, which is the expected product. It was identified as the product from the Friedel-Crafts alkylation reaction of toluene with benzyl chloride. It was explained that the tertiary organic phosphine was reacted with benzyl chloride to give the corresponding phosphonium chloride at the reaction temperature around 150° C., and then decomposed to produce benzyl cations at the higher temperature around 200° C., which reacted with toluene to give the electrophilic substitution reaction product of benzyltoluene. When a tertiary organic phosphine or an organic phosphonium chloride was used as a catalyst, the Friedel-Crafts alkylation reaction of arene compounds with alkyl halides_occurred, in which HX was generated by taking a halogen from the alkyl halide reactant and hydrogen from the arene ring, thereby the present invention is completed. In addition, since organic phosphonium chloride catalysts have different physical properties from reactants or products, the catalysts are not soluble in the products mixture and easy to recover for the reuse. It is known that the allyl halide or benzyl halide compound used in the Friedel-Crafts alkylation reaction gives cations stabilized by the functional group of vinyl or phenyl group. Furthermore, alkyl arene compounds may also be synthesized by the Friedel-Crafts alkylation reaction with unactivated alkyl halides having no functional group bonded to the halogen-substituted methylene group. The present invention based on such facts has the following object.

PURPOSE OF THE INVENTION

The present invention has been made in an effort to provide alkyl arene compounds synthesized by the Friedel-Crafts alkylation reaction of arene compounds with alkyl halide compounds using organic phosphine compounds as a catalyst, and a method for producing the same.

SUMMARY OF THE INVENTION

According to a suitable embodiment of the present invention, alkyl arene compounds are represented by Formulae 3-1, 3-2, and 3-3,

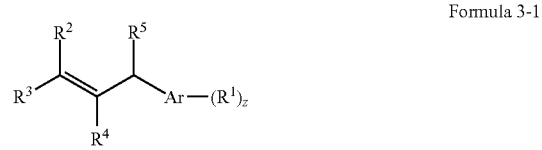

Formula 3-1

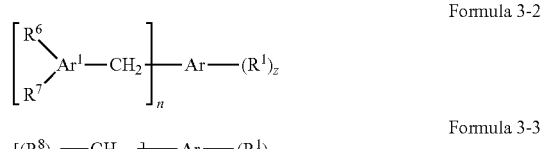

Formula 3-2

$$[(R^8)_y\text{—}CH_{3\text{-}y}\text{]}_m\text{—}Ar\text{—}(R^1)_z$$

Formula 3-3 in Formulae 3-1, 3-2, and 3-3, Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; $R^1$=F, Cl, Br, I, an alkyl group or phenyl group including an alkyl group or phenyl group having 1 to 8 carbon atoms, a diphenyl methyl group; $R^2$=H, Me, $CH_2Cl$, or $CH_2Br$; $R^3$=H, Me, Ph, $CH_2Cl$, or $CH_2Br$; $R^4$=H, Me, $CH_2Cl$, or $CH_2Br$; $R^5$=H or Me; $R^6$=H, a C1 to C4 alkyl group, or a phenyl group; $R^7$=H, F, Cl, Br, a C1 to C4 alkyl group, or $(CH_2)_qSi(R^\alpha)_p(OR^\beta)_{3-p}$ (q=1 to 10, $R^\alpha$=Cl or $CH_3$, p=0, 1, 2, 3, $R^\beta$=$CH_3$ or $C_2H_5$); $Ar^1$=benzene, naphthalene, anthracene, phenanthrene, pyrene, perylene, biphenyl, biphenyl ether, or biphenyl sulfide; $R^8$=an alkyl group having 1 to 10 carbon atoms or $(CH_2)_qSi(R^\alpha)_p(OR^\beta)_{3-p}$ (q=1 to 10, $R^\alpha$=Cl or $CH_3$, p=0, 1, 2, 3, $R^\beta$=$CH_3$ or $C_2H_5$); n=1 or 2; y=0, 1, 2 or 3; m=1, 2 or 3; when z=0, 1, 2, 3, 4, or 5 and z≠0, each $R^1$ may have the same or different structure.

According to another suitable embodiment of the present invention, a method for producing alkyl arene compounds represented by Formula 3-1, 3-2, or 3-3, is illustrated by the reaction of arene compounds represented by Formula 1 with alkyl halide compounds of Formulae 2-1, 2-2, and 2-3 using organic phosphine compounds represented by Formula 4, 5, or 6 as a catalyst,

            Formula 1

In Formula 1, Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; $R^1$=F, Cl, Br, I, an alkyl group or phenyl group including an alkyl group or phenyl group having 1 to 8 carbon atoms, a diphenyl methyl group; when z=0, 1, 2, 3, 4, or 5 and z≠0, each $R^1$ may have the same or different structure.

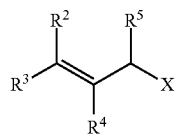            Formula 2-1

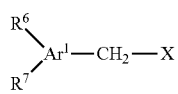            Formula 2-2

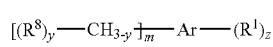            Formula 2-3

In Formulae 2-1, 2-2, and 2-3, $R^2$=H, Me, $CH_2Cl$ or $CH_2Br$; $R^3$=H, Me, Ph, $CH_2Cl$, or $CH_2Br$; $R^4$=H, Me, $CH_2Cl$, or $CH_2Br$; $R^5$=H or Me; $R^6$=H, a C1 to C4 alkyl group, or a phenyl group; $R^7$=H, F, Cl, Br, a C1 to C4 alkyl group, or $(CH_2)_qSi(R^\alpha)_p(OR^\beta)_{3-p}$ (q=1 to 10, $R^\alpha$=Cl or $CH_3$, p=0, 1, 2, 3, $R^\beta$=$CH_3$ or $C_2H_5$); $Ar^1$=benzene, naphthalene, anthracene, phenanthrene, pyrene, perylene, biphenyl, biphenyl ether, or biphenyl sulfide; $R^8$=an alkyl group having 1 to 10 carbon atoms or $(CH_2)_qSi(R^\alpha)_p(OR^\beta)_{3-p}$ (q=1 to 10, $R^\alpha$=Cl or $CH_3$, p=0, 1, 2, 3, $R^\beta$=$CH_3$ or $C_2H_5$); n=1 or 2; y=0, 1, 2, or 3; X=Cl, Br, or I.

            Formula 4

            Formula 5

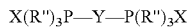            Formula 6

In Formulae 4, 5, and 6, R" may include a phenyl group while being an alkyl group or alkenyl group having 1 to 12 carbon atoms, and may be linked to each other by a covalent bond to have a cyclic structure, and each R" may have the same or different structure. R' is the same as $R^{2~8}$ in Formulae 2-1, 2-2, and 2-3, X=Cl, Br, or I, and Y may be an alkyl group or aryl group including an alkyl group or aryl group having 1 to 12 carbon atoms.

According to still another suitable embodiment of the present invention, one or more solvents selected from a hydrocarbon, ether, dimethoxyethane (DME), or THF may be used.

According to yet another suitable embodiment of the present invention, the reaction temperature is from 100° C. to 250° C.

According to still yet another suitable embodiment of the present invention, when compounds of Formula 1 and Formulae 2-1, 2-2, and 2-3 are in a liquid phase, the reactants may be used without any solvent.

According to a further suitable embodiment of the present invention, the concentration of the catalyst is from 5 to 20 mol % relative to the compounds of Formulae 2-1, 2-2, and 2-3.

DETAILED DESCRIPTION OF EXEMPLARY EMBODIMENTS

Exemplary embodiments of the present invention will be described herein below.

The present invention relates to processes for preparing the alkyl arene compounds represented by Formula 3-1 by the Friedel-Crafts alkylation reaction which comprise a dehydrohalogenation by taking a halogen from allyl halide compounds of Formula 2-1 and a hydrogen from arene compounds of Formula 1, using a tertiary organic phosphine of Formula 4 or a quaternary organic phosphonium salt of Formula 5 or 6 as a catalyst, as illustrated by Reaction Scheme 1 below.

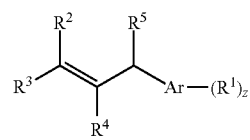            Formula 3-1

In Formula 3-1, Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; $R^1$=F, Cl, Br, I, an alkyl group or phenyl group including an alkyl group or phenyl group having 1 to 8 carbon atoms, a diphenyl methyl group; $R^2$=H, Me, $CH_2Cl$, or $CH_2Br$; $R^3$=H, Me, Ph, $CH_2Cl$, or $CH_2Br$; $R^4$=H, Me, $CH_2Cl$, or $CH_2Br$; $R^5$=H or Me. When z=0, 1, 2, 3, 4, or 5 and z≠0, each $R^1$ may have the same or different structure.

Reaction Scheme 1

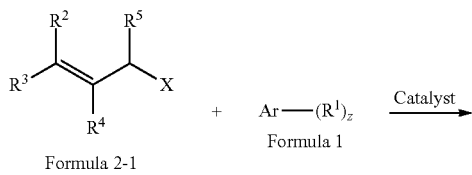

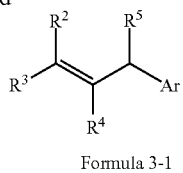

Formula 3-1

In Reaction Scheme 1, Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; $R^1$=F, Cl, Br, I, an alkyl group or phenyl group including an alkyl group or phenyl group having 1 to 8 carbon atoms, a diphenyl methyl group; $R^2$=H, Me, $CH_2Cl$, or $CH_2Br$; $R^3$=H, Me, Ph, $CH_2Cl$, or $CH_2Br$; $R^4$=H, Me, $CH_2Cl$, or $CH_2Br$; $R^5$=H or Me; X=Cl, Br, or I. When z=0, 1, 2, 3, 4, or 5 and z≠0, each $R^1$ may have the same or different structure.

The tertiary organic phosphine or the quaternary organic phosphonium salt used as a catalyst in Reaction Scheme 1 may be represented by, for example, Formula 4 and Formula 5 or 6, respectively.

  Formula 4

  Formula 5

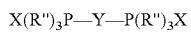  Formula 6

In Formulae 4, 5, and 6, R" may include a phenyl group while being an alkyl group or alkenyl group having 1 to 12 carbon atoms, and may be linked to each other by a covalent bond to have a cyclic structure, and each R" may have the same or different structure. R' is the same as $R^{2\sim8}$ in Formulae 2-1, 2-2, and 2-3, X=Cl, Br, or I, and Y may be an alkyl group or aryl group including an alkyl group or aryl group having 1 to 12 carbon atoms.

The tertiary organic phosphine serving as a catalyst may include one or more compounds selected from among trimethylphosphine, triethylphosphine, tributhylphosphine, methyldiphenylphosphine, tricyclohexylphosphine, triisopropylphosphine, tripropylphosphine, dimethylphenylphosphine, ethyldiphenylphosphine, t-butyldiphenylphosphine, t-butyldiisopropylphosphine, isopropyldiphenylphosphine, dicyclohexylphenylphosphine, benzyldiphenylphosphine, cyclohexyldiphenylphosphine, tricyclopentylphosphine, di-t-butylneopentylphosphine, di-t-butylphenylphosphine, di-t-butylmethylphosphine, and t-butyldicyclohexylphosphine.

The quaternary organic phosphonium salt may include one or more compounds selected from among benzyltributylphosphonium chloride, tetrabutylphosphonium chloride, tetrabutylphosphonium bromide, tetrabutylphosphonium iodide, tetramethylphosphonium bromide, tetraethylphosphonium chloride, (4-ethylbenzyl)triphenylphosphonium chloride, hexyltriphenylphosphonium chloride, benzyltriphenylphosphonium chloride, tetraphenylphosphonium chloride, bis(benzyldimethylphosphonium chloride)ethane, bis(benzyldimethylphosphonium chloride) butane or silica or a silicone resin, silicone silsequioxane, and a quaternary alkylphosphonium chloride immobilized on an organic polymer.

In the preparation of allyl arene compounds, when arene compounds are reacted with allyl halides using a Lewis acid catalyst such as aluminum, boron, iron or copper chlorides. Arene compounds substituted with haloalkyl group instead of allyl group may be produced (Roberts, R. M.; Khalaf, A. A. *Friedel-Crafts Alkylation Chemistry. A Century of Discovery;* Marcel Dekker: New York, 1984, 465-467). In contrast, when a tertiary organic phosphine or a quaternary organic phosphonium salt which is neutral is used as a catalyst for the Friedel-Crafts alkylation reaction, allyl arene compounds are produced, and the catalyst may be easily recovered and reused. According to the present invention, since the boiling point of allyl halide is lower than the reaction temperature around 200° C., it is difficult to react allyl halide under atmospheric pressure, and it is recommended to use a reaction vessel useful for a high-pressure reaction.

In a typical preparation, the allyl halide compounds represented by Formula 2-1 and arene compounds of Formula 1 and a tertiary organic phosphine or a quaternary organic phosphonium salt catalyst are placed all together in a high-pressure reaction vessel under inert atmosphere. The amount of allyl halide compounds of Formula 2-1 is used, generally 1 to 100 mol %, preferably 5 to 50 mol %, relative to the amount of the arene compounds of Formula 1. The tertiary organic phosphine or quaternary organic phosphonium salt is used as a catalyst in an amount of sufficient to catalyze the reaction, generally 1 to 100 mol %, preferably 5 to 50 mol %, relative to the moles of compounds of Formula 2-1. After sealing the reaction vessel, heating may be applied for a certain period of time, generally 1 hr to about 48 hours, to complete the reaction. The reaction is carried out at a temperature from 100° C. to 250° C., preferably 150° C. to 220° C. The tertiary organic phosphine used as a catalyst in such a reaction process reacts with allyl halides during the reaction to become a quaternary organic phosphine chloride salt. The quaternary organic phosphonium salt used as a catalyst has excellent activity and becomes a salt compound, so that the quaternary organic phosphonium salt has different physical properties from the reactant or product, and thus can be easily separated and reused. Therefore, it is advantageous to synthesize the alkyl arene compounds of Formula 3-1 by reacting the allyl halides of Formula 2-1 with the arene compounds of Formula 1 using the tertiary organic phosphine or the quaternary organic phosphonium salt as a catalyst. The reaction solvent may be appropriately selected depending on the reactant, for example, a reaction solvent such as an aliphatic hydrocarbon, or a solvent such as ether, dimethoxyethane (DME), or THF may be used. The reaction may be carried out in the absence of a reaction solvent. When cyclic THF is used as a solvent, the ring of THF may be opened by HX, the byproduct and halobutyl alcohol may be produced, and the condensation reaction of such alcohol to give halobutyl ether may be resulted. After the product of Formula 3-1 is separated from the product mixture, the product catalyst may be separated for recycling. The recovery rate may be at the level of 80 wt % of the amount of catalyst used, which is very economically advantageous. When the organic phosphonium salt immobilized on a silicone resin, silica, or zeolite is used, it is very convenient to recover and reuse the catalyst after the reaction.

The allyl halide of Formula 2-1 for the reaction may include the following compounds:

allyl chloride, allyl bromide, allyl iodide, 3-chloro-1-butene, 3-bromo-1-butene, 3-iodo-1-butene, 1-chloro-2-butene, 1-bromo-2-butene, 1-iodo-2-butene, 3-chloro-2-methyl-1-propene, 3-bromo-2-methyl-1-propene, 3-iodo-2-methyl-1-propene, (3-chloro-propenyl)benzene, (3-bromo-propenyl)benzene, (3-iodo-propenyl)benzene, 1,4-dichloro-2-butene, 1,4-dibromo-2-butene.

All of these compounds may be either commercially produced or easily synthesized.

The compound represented by Formula 1 may include compounds which may be either commercially produced or easily synthesized, such as:

benzene, toluene, o-xylene, m-xylene, p-xylene, mesitylene, ethylbenzene, propylbenzene, n-butylbenzene, isobutylbenzene, t-butylbenzene, 1,2,4,5-tetramethylbenzene, fluorobenzene, bromobenzene, iodobenzene, anisole, biphenyl, fluorene, o-terphenylene, m-terphenylene, p-terphenylene, naphthalene, 1-methylnaphthalene, 1-methyl-2-methylnaphthalene, biphenyl, biphenyl ether, biphenyl sulfide, anthracene, 9-bromoanthracene, 9-methylanthracene, 9,10-dimethylanthracene, pyrene, 1,6-dimethylpyrene, 2,7-dimethylpyrene, 1,6-diphenylpyrene, 2,7-dibenzylpyrene, 2,7-bis(diphenylmethyl)pyrene, triphenylene, perylene, dimethylperylene, tetracene, pentacene.

Since the allyl halides of Formula 2-1 may be substituted with as many as the number of hydrogens bonded to the ring of the arene compound of Formula 1, various forms of products may be obtained depending on the reaction molar proportion. When the allyl halides of Formula 2-1 are used in excess, a number of allyl groups may be substituted in the arene compounds of Formula 1, and when the allyl halides of Formula 2-1 are used in an appropriate amount, it is possible to obtain Formula 3-1 in which allyl groups as many as the number of hydrogens bonded to the ring are substituted. Since an allyl group substituted with an arene compound having two or more rings may form a hexagonal ring through the alkylation of allyl group with the arene ring, a compound having an increased number of arene rings may be obtained. In contrast, when the arene compounds of Formula 1 are used in excess relative to allyl halides, a compound in which one allyl group is substituted may be obtained as a main product.

The tertiary organic phosphine or the quaternary organic phosphonium salt used as a catalyst may be represented by, for example, Formula 4 and Formula 5 or 6, respectively. The quaternary organic phosphonium salt used as a catalyst can be easily recovered from the reaction mixture, and for example, when the reaction product is distilled under reduced pressure after the reaction is completed, the catalyst remains as solid, and thus can be conveniently recovered. The catalyst could be recovered to a level of about 80% of the amount of catalyst initially used, and the recovered catalyst may be recrystallized with a suitable solvent, and thus reused. In the reaction process, the tertiary organic phosphine or quaternary organic phosphonium salt as a catalyst is used generally, 1 to 100 mol %, preferably 5 to 20 mol %, relative to the moles of the arene compound of Formula 1, and when the reaction is performed at a temperature from 100° C. to 250° C., preferably 150° C. to 220° C., and the reaction may be completed within generally 1 hr to 48 hr, allyl arene compounds represented by Formula 3-1 of Reaction Scheme 1 could be obtained. The tertiary organic phosphine used as a catalyst in such a reaction process reacts with allyl halide in the reaction process to give the corresponding quaternary organic phosphine chloride salt. The quaternary organic phosphonium salt used as a catalyst shows excellent activity and has different physical properties from the reactants or products, so that the quaternary organic phosphonium salt can be easily separated and reused. The reaction may be run without any solvent and a hydrocarbon or dimethoxyethane (DME) may be selectively used as a reaction solvent. When the reaction is completed, a compound represented by Formula 3-1 may be obtained by distillation under atmospheric pressure or reduced pressure. Hereinafter, examples for producing compounds according to the present invention will be described.

Example 1

Example 1-1: Synthesis of Allylbenzene 50 g (0.64 mol) of benzene, 24.5 g (0.32 mol) of allyl chloride, and 9.4 g (0.032 mol) of tetrabutylphosphonium chloride, 10 mol % of the number of moles of the allyl chloride were placed into a high temperature and high pressure reaction vessel made of a stainless steel tube having a volume of 290 ml under inert atmosphere, and the reaction mixture was reacted at 200° C. for 5 hours. This solution was taken out into a round bottom flask and distilled under reduced pressure to obtain 18.7 g (0.16 mol, yield 49.5%) of allylbenzene. As a result of 300 MHz hydrogen nuclear magnetic resonance analysis of the obtained product, $C-CH_2-C$, $CH_2=C$, $C-CH=C$, and Ph were confirmed at 3.3 ppm (d, 2H), 4.8 to 5.1 ppm (m, 2H), 5.9 ppm (m, 1H), and 7.1 to 7.3 ppm (m, 5H), respectively.

Example 1-2: Synthesis of 1,3-diphenyl-1-propene 50 g (0.64 mol) of benzene, 48.8 g (0.32 mol) of cinnamyl chloride, and 9.4 g (0.032 mol) of tetrabutylphosphonium chloride were placed into the reaction vessel and under inert atmosphere and reacted at 200° C. for 5 hours in the same manner as in Example 1-1 to obtain 41.9 g (0.22 mol, yield 67.4%) of 1,3-diphenyl-1-propene. As a result of 300 MHz hydrogen nuclear magnetic resonance analysis of the obtained product, $C-CH_2-C$, $C=CH-C$, $C-CH=C$, and Ph were confirmed at 3.3 ppm (d, 2H), 6.3 ppm (d, 1H), 6.7 ppm (m, 1H), and 7.2 to 7.3 ppm (m, 10H), respectively.

Example 1-3: Synthesis of 1-allyl naphthalene 50 g (0.39 mol) of naphthalene, 14.9 g (0.20 mol) of allyl chloride, 5.7 g (0.02 mol) of tetrabutylphosphonium chloride, and 60 ml of decane were reacted at 200° C. for 6 hours in the same manner as in Example 1-1 to obtain 25.3 g (0.15 mol, 77.1%) of 1-allyl napthalene. As a result of 300 MHz hydrogen nuclear magnetic resonance analysis of the obtained product, $C-CH_2-C$, $CH_2=C$, $C-CH=C$, and a Naph peak were confirmed at 3.7 ppm (d, 2H), 5.0 ppm (m, 2H), 6.3 ppm (m, 1H), and 7.1 to 7.8 ppm (m, 7H), respectively. Furthermore, it was confirmed by GC/MS analysis that as byproducts, diallyl naphthalene, and dihydropyrene which is a compound in which hydrogen was released from diallyl naphthalene and the remaining components were cyclized, were produced.

Example 1-4: Synthesis of 1-(2-methylallyl)naphthalene 40 g (0.31 mol) of naphthalene, 14.1 (0.16 mol) g of 3-chloro-2-methyl-1-propene, 5.4 g (0.016 mol) of tetrabutylphosphonium bromide, and 60 ml of decane were reacted at 200° C. for 6 hours in the same manner as in Example 1-1 to obtain 22.8 g of (0.12 mol, yield 80.2%) of 1-(2-methylallyl)naphthalene. As a result of 300 MHz hydrogen nuclear magnetic resonance analysis of the obtained product, $CH_3-C$, $C-CH_2-C$, $CH_2=C$, and a. Naph peak were confirmed at 1.7 ppm (s, 3H), 3.7 ppm (s, 2H), 4.7 ppm (m, 2H), and 7.1 to 7.8 ppm (m, 7H), respectively.

Example 1-5: Synthesis of 1-cinnamyl naphthalene 30 g (0.23 mol) of naphthalene, 17.9 g (0.12 mol) of cinnamyl chloride, 4.1 g (0.012 mol) of tetrabutylphosphonium bromide, and 60 ml of decane were reacted at 200° C. for 6 hours in the same manner as in Example 1-1 to obtain 20.4 g (0.08 mol, yield 69.7%) of 1-cinnamyl naphthalene. As a result of 300 MHz hydrogen nuclear magnetic resonance analysis of the obtained product, C—$CH_2$—C, C=CH—C, C—CH=C, and a Naph peak were confirmed at 3.7 ppm (d, 2H), 6.3 ppm (d, 1H), 6.7 ppm (m, 1H), and 7.1 to 7.8 ppm (m, 12H), respectively.

Example 1-6: Synthesis of 1-allyl-5-bromonaphthalene 50 g (0.24 mol) of 1-bromonaphthalene, 9.2 g (0.12 mol) of allyl chloride, 3.5 g (0.012 mol) of tetrabutylphosphonium chloride, and 50 ml of THF were reacted at 200° C. for 6 hours in the same manner as in Example 1-1 to obtain 18.5 g (0.07 mol, yield 62.3%) of 1-allyl-5-bromonaphthalene. As a result of 300 MHz hydrogen nuclear magnetic resonance analysis of the obtained product, C—$CH_2$—C, $CH_2$=C, C=CH—C, and a Naph peak were confirmed at 3.8 ppm (d, 2H), 5.0 ppm (m, 2H), 6.0 ppm (m, 1H), and 7.0 to 8.0 ppm (m, 6H), respectively.

Example 1-7: Synthesis of 1-bromo-5-(2-butenyl)naphthalene 50 g (0.24 mol) of 1-bromonaphthalene, 10.9 g (0.12 mol) of 1-chloro-2-butene, 3.5 g (0.012 mol) of tetrabutylphosphonium chloride, and 50 ml of THF 50 ml were reacted at 200° C. for 6 hours in the same manner as in Example 1-1 to obtain 20.4 g (0.08 mol, yield 65%) of 1-bromo-5-(2-butenyl)naphthalene. As a result of 300 MHz hydrogen nuclear magnetic resonance analysis of the obtained product, $CH_3$—C, C—$CH_2$—C, C—CH=C, C=CH—C, and a Naph peak were confirmed at 1.6 ppm (d, 3H), 3.8 ppm (d, 2H), 5.4 ppm (m, 1H), 6.0 ppm (m, 1H), and 7.0 to 8.1 ppm (m, 6H).

Example 1-8: Synthesis of 9-allyl anthracene 40 g (0.22 mol) of anthracene, 8.6 g (0.11 mol) of allyl chloride, 3.2 g (0.011 mol) of tetrabutylphosphonium chloride, and 50 ml of THF were reacted at 200° C. for 5 hours in the same manner as in Example 1-1 to obtain 14.9 g (0.07 mol, yield 62.1%) of 9-allyl anthracene. As a result of 300 MHz hydrogen nuclear magnetic resonance analysis of the obtained product, Anth-$CH_2$—C, $CH_2$=C, C—CH=C, and an Anth peak were confirmed at 3.8 ppm (d, 2H), 5.0 ppm (m, 2H), 6.0 ppm (m, 1H), and 7.5 to 8.3 ppm (m, 9H).

Example 1-9: Synthesis of 9-(1-methyl-2-propenyl)anthracene 40 g (0.22 mol) of anthacene, 10 g (0.11 mol) of 3-chloro-1-butene, 3.2 g (0.011 mol) of tetrabutylphosphonium chloride, and 50 ml of THF were reacted at 200° C. for 5 hours in the same manner as in Example 1-1 to obtain 17.8 g (0.08 mol, yield 69.7%) of 9-(1-methyl-2-propenyl)anthracene. As a result of 300 MHz hydrogen nuclear magnetic resonance analysis of the obtained product, $CH_3$—C, C—CH=C, C, $CH_2$=C, C—CH=C, and an Anth peak were confirmed at 1.4 ppm (d, 3H), 3.6 ppm (m, 1H), 5.0 ppm (m, 2H), 6.3 ppm (m, 1H), and 7.5 to 8.3 ppm (m, 9H), respectively.

Example 1-10: Synthesis of 9-cinnamyl anthracene 40 g (0.22 mol) of anthracene, 16.8 g (0.11 mol) of cinnamyl chloride, 3.2 g (0.011 mol) of tetrabutylphosphonium chloride, and 50 ml of THF were reacted at 200° C. for 5 hours in the same manner as in Example 1-1 to obtain 18.8 g (0.06 mol, yield 58.2%) of 9-cinnamyl anthracene. As a result of 300 MHz hydrogen nuclear magnetic resonance analysis of the obtained product, C—$CH_2$—C, C=CH-Ph, C—CH=C, Pf and an Anth peak were confirmed at 3.8 ppm (d, 2H), 6.3 ppm (d, 1H), 6.7 ppm (m, 1H), 7.2 to 7.3 ppm (m, 5H), and 7.5 to 8.3 ppm (m, 9H), respectively.

Example 11: Synthesis of diallyl anthracene 30 g (0.17 mol) of anthracene, 38.63 g (0.50 mol) of allyl chloride, 7.4 g (0.025 mol) of tetrabutylphosphonium chloride, and 50 ml of THF were reacted at 200° C. for 5 hours in the same manner as in Example 1-1 to obtain 18.7 g (0.07 mol, yield 43%) of diallyl anthracene.

The obtained compound was analyzed through GC/MS and confirmed to contain isomers. In addition, it was confirmed that dihydroperylene, which is a cyclized compound, was produced.

Example 1-12: Synthesis of 3-allyl anthrone 30 g (0.15 mol) of anthrone, 5.9 g (0.08 mol) of allyl chloride, 3.1 g (0.008 mol) of benzyltriphenylphosphonium chloride, and 50 ml of DME were reacted at 200° C. for 5 hours in the same manner as in Example 1-1 to obtain 13.5 g (0.06 mol, yield 72%) of 3-allyl anthrone. As a result of 300 MHz hydrogen nuclear magnetic resonance analysis of the obtained product, C—$CH_2$—C, Ph-CTA-Ph. $CH_2$=C, C=CH—C, and a Ph peak were confirmed at 3.3 ppm (d, 2H), 4.4 ppm (s, 2H), 4.8 to 5.0 ppm (m, 2H), 6.0 ppm (m, 1H), and 7.4 to 8.4 ppm (m, 7H), respectively.

Example 1-13: Synthesis of 3,6-diallyl anthrone 30 g (0.15 mol) of anthrone, 35.5 g (0.46 mol) of allyl chloride, 6.2 g (0.016 mol) of benzyltriphenylphosphonium chloride, and 30 ml of DME were reacted at 200° C. for 7 hours in the same manner as in Example 1-1 to obtain 22.5 g (0.08 mol, yield 54.6%) of 3,6-diallyl anthrone. As a result of 300 MHz hydrogen nuclear magnetic resonance analysis of the obtained product, C—$CH_2$—C, Ph-$CH_2$-Ph. $CH_2$=C, C=CH—C, and a Ph peak were confirmed at 3.3 ppm (d, 4H), 4.4 ppm (s, 2H), 5.0 ppm (m, 4H), 6.0 ppm (m, 2H), and 7.4 to 7.7 ppm (m, 6H), respectively.

Example 1-14: Synthesis of 3-(2-methylallyl)anthrone 30 g (0.15 mol) of anthrone, 7.2 g (0.08 mol) of 3-chloro-2-methyl-propene, 2.4 g (0.008 mol) of tetrabutylphosphonium chloride, and 40 ml of DME were put into the reaction vessel and reacted at 200° C. for 5 hours in the same manner as in Example 1-1 to obtain 13.2 g (0.05 mol, yield 66.2%) of 3-(2-methylallyl)anthrone. As a result of 300 MHz hydrogen nuclear magnetic resonance analysis of the obtained product, $CH_3$—C, C—$CH_2$—C, Ph-$CH_2$-Ph, $CH_2$=C, and a Ph peak were confirmed at 1.8 ppm (s, 3H), 3.2 ppm (s, 2H), 4.4 ppm (s, 2H), 5.0 ppm (d, 2H), and 7.4 to 8.4 ppm (m, 7H), respectively.

Example 1-15: Synthesis of 1-allylpyrene 40 g (0.19 mol) of pyrene, 7.6 g (0.10 mol) of allyl chloride, 2.9 g (0.01 mol) of tetrabutylphosphonium chloride, and 50 ml of THF were reacted at 200° C. for 5 hours in the same manner as in Example 1-1 to obtain 19.1 g (0.08 mol, yield 78.8%) of 1-allylpyrene. As a result of 300 MHz hydrogen nuclear magnetic resonance analysis of the obtained product, C—CH$_2$—C, CH$_2$=C, C=CH—C, and a Pyrene peak were confirmed at 3.7 ppm (d, 2H), 4.8 to 5.0 ppm (m, 2H), 6.0 ppm (m, 1H), and 7.7 to 8.3 ppm (m, 9H), respectively.

Example 1-16: Synthesis of 2-(3-butenyl)pyrene 40 g (0.19 mol) of pyrene, 9.1 g (0.10 mol) of 3-chloro-1-butene, 2.9 g (0.01 mol) of tetrabutylphosphonium chloride, and 50 ml of THF were reacted at 200° C. for 5 hours in the same manner as in Example 1-1 to obtain 19.2 g of 1-(2-(3-butenyl))pyrene (0.07 mol, yield 74.9%). As a result of 300 MHz hydrogen nuclear magnetic resonance analysis of the obtained product, CH$_3$—C, C—CH—C, CH$_2$=C, C=CH—C, and a Pyrene peak were confirmed at 1.4 ppm (d, 3H), 3.6 ppm (m, 1H), 5.0 ppm (m, 2H), 6.3 ppm (m, 1H), and 7.7 to 8.3 ppm (m, 9H), respectively.

Example 1-17: Synthesis of 1-cinnamyl pyrene 40 g (0.19 mol) of pyrene, 15.3 g (0.10 mol) of cinnamyl chloride, 2.9 g (0.01 mol) of tetrabuylphosphonium chloride, and 50 ml of THF were reacted at 200° C. for 5 hours in the same manner as in Example 1-1 to obtain 24.5 g (0.08 mol, yield 77%) of 1-cinnamyl pyrene. As a result of 300 MHz hydrogen nuclear magnetic resonance analysis of the obtained product, C—CH$_2$—C, C—CH=C, Ph, and a Pyrene peak were confirmed at 3.8 ppm (d, 2H), 6.4 to 6.7 ppm (m, 2H). 7.2 to 7.3 ppm (m, 5H), and 7.7 to 8.3 ppm (m, 9H), respectively.

Example 1-18: Synthesis of 1-(2-methylallyl)pyrene 40 g (0.19 mol) of pyrene, 9.1 g (0.10 mol) of 3-chloro-2-methyl-1-propene, 2.9 g (0.10 mol) of tetrabutylphosphonium chloride, and 50 ml of THF were reacted at 200° C. for 5 hours in the same manner as in Example 1-1 to obtain 20.3 g (0.08 mol, yield 79.2%) of 1-(2-methylallyl)pyrene. As a result of 300 MHz hydrogen nuclear magnetic resonance analysis of the obtained product, CH$_3$—C, C—CH$_2$—C, CH$_2$=C, and a Pyrene peak were confirmed at 1.8 ppm (s, 3H), 3.7 ppm (s, 2H), 4.9 to 5.0 ppm (d, 2H), and 7.7 to 8.3 ppm (m, 9H).

Example 1-19: Synthesis of 1-(2-butenyl)pyrene 40 g (0.19 mol) of pyrene, 9.1 g (0.10 mol) of 1-chloro-2-butene, 2.9 g (0.01 mol) of tetrabutylphosphonium chloride, and 50 ml of THF were reacted at 200° C. for 5 hours in the same manner as in Example 1-1 to obtain 20.2 g (0.08 mol, yield 78.9%) of 1-(2-butenyl)pyrene. As a result of 300 MHz hydrogen nuclear magnetic resonance analysis of the obtained product, CH$_3$—C, C—CH$_2$—C, C—CH=C, C=CH—C, and a Pyrene peak were confirmed at 1.8 ppm (d, 3H), 3.7 ppm (d, 2H), 5.4 ppm (m, 1H), 6.1 ppm (m, 1H), and 7.7 to 8.3 ppm (m, 9H), respectively.

Example 1-20: Synthesis of 2-(t-butyl)-10-allylanthracene 40 g (0.17 mol) of 2-(t-butyl)anthracene, 6.5 g (0.09 mol) of allyl chloride, 2.7 g (0.009 mol) of tetrabutylphosphonium chloride, and 50 ml of THF were reacted at 200° C. for 6 hours in the same manner as in Example 1-1 to obtain 17.5 g (0.06 mol, yield 71%) of 2-(t-butyl)-10-allylanthracene. As a result of 300 MHz hydrogen nuclear magnetic resonance analysis of the obtained product, CH$_3$—C, C—CH$_2$—C, CH$_2$=C, C—CH=C, and an Anth peak were confirmed at 1.5 ppm (s, 9H), 3.8 ppm (d, 2H), 4.8 to 5.0 ppm (m, 2H), 6.0 ppm (m, 1H), and 7.4 to 8.3 ppm (m, 8H), respectively.

Example 1-21: Synthesis of 2-(t-butyl)-10-(2-butenyl)anthracene 40 g (0.17 mol) of 2-(t-butyl)anthracene, 8.1 g (0.09 mol) of 1-chloro-2-butene, 2.7 g (0.009 mol) of tetrabutylphosphonium chloride, and 50 ml of THF were reacted at 200° C. for 6 hours in the same manner as in Example 1-1 to obtain 18.2 g (0.06 mol, yield 70.2%) of 2-(t-butyl)-10-(2-butenyl)anthracene. As a result of 300 MHz hydrogen nuclear magnetic resonance analysis of the obtained product, CH$_3$—C, CH$_3$—C, C—CH$_2$—C, C—CH=C, C=CH—C. and an Anth peak were confirmed at 1.5 ppm (s, 9H), 1.7 ppm (d, 1H), 3.8 ppm (d, 2H), 5.4 ppm (m, 1H), 6.1 ppm (m, 1H), and 7.4 to 8.3 ppm (m, 8H), respectively.

Example 1-22: Synthesis of 10-allyl-9-methylanthracene 40 g (0.20 mol) of 9-methylanthracene, 8.0 g (0.10 mol) of allyl chloride, 3.0 g (0.01 mol) of tetrabutylphosphonium chloride, and 50 ml of THF were reacted at 200° C. for 6 hours in the same manner as in Example 1-1 to obtain 18.7 g (0.08 mol, yield 80%) of 10-allyl-9-methylanthracene. As a result of 300 MHz hydrogen nuclear magnetic resonance analysis of the obtained product, C—CH$_3$, C—CH$_2$—C, CH$_2$=C, C=CH—C, and an Anth peak were confirmed at 2.7 ppm (s, 3H), 3.8 ppm (d, 2H), 4.8 to 5.0 ppm (m, 2H), 6.0 ppm (m, 1H), and 7.5 to 8.2 ppm (m, 8H).

Example 1-23: Synthesis of 10-cinnamyl-9-methylanthracene 40 g (0.20 mol) of 9-methylanthracene, 15.3 g (0.10 mol) of cinnamyl chloride, 3.0 g (0.01 mol) of tetrabutylphosphonium chloride, and 50 ml of THF 50 ml were reacted at 200° C. for 6 hours in the same manner as in Example 1-1 to obtain 21.2 g (0.07 mol, yield 68.7%) of 10-cinnamyl-9-methylanthracene. As a result of 300 MHz hydrogen nuclear magnetic resonance analysis of the obtained product, C—CH$_3$, C—CH$_2$—C, C=CH-Ph. C—CH=C, Ph, and an Anth peak were confirmed at 2.7 ppm (s, 3H), 3.8 ppm (d, 2H), 6.4 ppm (d, 1H), 6.7 ppm (m, 1H), 7.2 to 7.3 ppm (m, 5H), and 7.5 to 8.2 ppm (m, 8H), respectively.

Example 1-24: Synthesis of 1-allyl-4-phenoxy ether 60 g (0.35 mol) of diphenyl ether, 13.5 g (0.18 mol) of allyl chloride, and 5.2 g (0.018 mol) of tetrabutylphosphonium chloride were reacted at 200° C. for 7 hours in the same manner as in Example 1-1 to obtain 24.3 g (0.12 mol, yield 64.2%) of 1-allyl-4-phenoxy ether. As a result of 300 MHz hydrogen nuclear magnetic resonance analysis of the obtained product, C—CH$_2$—C, CH$_2$=C, C=CH—C, and a Ph peak were confirmed at 3.3 ppm (d, 2H), 5.0 ppm (m, 2H), 5.9 ppm (m, 1H), and 7.1 to 7.4 ppm (m, 9H), respectively.

Example 1-25: Synthesis of 1-(2-butenyl)-4-phenoxy ether 60 g (0.35 mol) of diphenyl ether, 16.3 g (0.18 mol) of 1-chloro-2-butene, and 5.2 g (0.018 mol) of tetrabutylphosphonium chloride were reacted at 200° C. for 7 hours in the same manner as in Example 1-1 to obtain 24.3 g (0.11 mol, yield 60.3%) of 1-(2-butenyl)-4-phenoxy ether. As a result of 300 MHz hydrogen nuclear magnetic resonance analysis of the obtained product, CH$_3$—C, C—CH$_2$—C, C—CH=C, C=CH—C, and a Ph peak were confirmed at 1.7 ppm (d, 3H), 3.3 ppm (d, 2H), 5.4 ppm (m, 1H), 6.1 ppm (m, 1H), and 7.1 to 7.4 ppm (m, 9H), respectively.

Example 1-26: Synthesis of 2-(3-butenyl)-4-phenoxy ether 60 g (0.35 mol) of diphenyl ether, 16.3 g (0.18 mol) of 1-chloro-2-butene, and 5.2 g (0.018 mol) of tetrabutylphosphonium chloride were reacted at 200° C. for 7 hours in the same manner as in Example 1-1 to obtain 28.7 g (0.13 mol, yield 71%) of 1-(2-(3-butenyl))-4-phenoxy ether. As a result of 300 MHz hydrogen nuclear magnetic resonance analysis of the obtained product, CH$_3$—C, C—CH—C, CH$_2$=C, C=CH—C, and a Ph peak were confirmed at 1.4 ppm (d, 3H), 3.6 ppm (m, 1H), 5.0 ppm (m, 2H), 6.3 ppm (m, 1H), and 7.1 to 7.4 ppm (m, 9H), respectively.

The present invention relates to processes for preparing the alkyl arene compounds represented by Formula 3-2 by the Friedel-Crafts alkylation reaction which comprises a dehydrohalogenation by taking a halogen from halomethyl arene compounds of Formula 2-2 and a hydrogen from arene compounds of Formula 1, using a tertiary organic phosphine of Formula 4 or a quaternary organic phosphonium salt of Formula 5 or 6 as a catalyst, illustrated by Reaction Scheme 2 below.

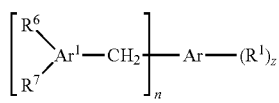

Formula 3-2

In Formula 3-2, Ar$^1$=benzene, naphthalene, anthracene, phenanthrene, pyrene, perylene, biphenyl, biphenyl ether, or biphenyl sulfide; R$^6$=H, a C1 to C4 alkyl group or a phenyl group; R$^7$=H, F, Cl, Br, a C1 to C4 alkyl group or (CH$_2$)$_q$Si(R$^\alpha$)$_p$(OR$^\beta$)$_{3-p}$ (q=1 to 10, R$^\alpha$=Cl or CH$_3$, p=0, 1, 2, 3, R$^\beta$=CH$_3$ or C$_2$H$_5$); Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; R$^1$=F, Cl, Br, I, an alkyl group or phenyl group including an alkyl group or phenyl group having 1 to 8 carbon atoms; a diphenyl methyl group, and n=1 or 2; when z=0, 1, 2, 3, 4, or 5 and z≠0, each R$^1$ may have the same or different structure.

Reaction Scheme 2

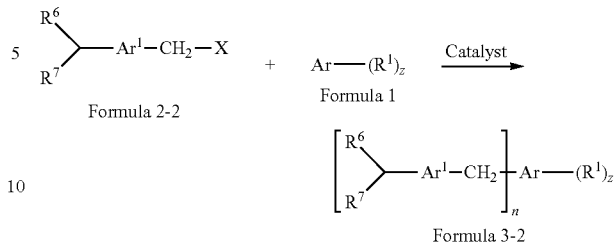

In Reaction Scheme 2, Ar$^1$=benzene, naphthalene, anthracene, phenanthrene, pyrene, perylene, biphenyl, biphenyl ether, or biphenyl sulfide; R$^6$=H, a C1 to C4 alkyl group, or a phenyl group; R$^7$=H, F, Cl, Br, a C1 to C4 alkyl group, or (CH$_2$)$_q$Si(R$^\alpha$)$_p$(OR$^\beta$)$_{3-p}$ (q=1 to 10, R$^\alpha$=Cl or CH$_3$, p=0, 1, 2, 3, R$^\beta$=CH$_3$ or C$_2$H$_5$); X=Cl, Br, or I; Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; R$^1$=F, Cl, Br, I, an alkyl group or phenyl group including an alkyl group or phenyl group having 1 to 8 carbon atoms; a diphenyl methyl group, and n=1 or 2; when z=0, 1, 2, 3, 4, or 5 and z≠0, each R$^1$ may have the same or different structure.

The tertiary organic phosphine or the quaternary organic phosphonium salt used as a catalyst in Reaction Scheme 2 may be represented by, for example, Formula 4 and Formula 5 or 6, respectively. All the compounds of Formulae 4, 5 and 6 are the same as the compounds described in Reaction Scheme 1 above.

In the process of producing (arylmethyl) arene compounds, the boiling point of the halomethyl arene compounds of Formula 2-2 or the arene compounds of Formula 1 are lower than the reaction temperature of 250° C., so that it is difficult to react the compound under atmospheric pressure, and the reaction needs to be performed under pressure.

In a typical preparation, the halomethyl arene compounds of Formula 2-2 and the arene compounds of Formula 1, and the tertiary organic phosphine or the quaternary organic phosphonium salt catalyst are placed all together in a high-pressure reaction vessel under inert atmosphere. The amount of the compounds of Formula 2-2 is used, generally 1 to 100 mol %, preferably 5 to 50 mol %, relative to the amount of the arene compounds of Formula 1. Thereafter, when the reaction mixture is heated to from 100° C. to 250° C., preferably 150° C. to 220° C., the alkyl arene compounds of Formula 3-2 of Reaction Scheme 2 could be synthesized. The tertiary organic phosphine or quaternary organic phosphine halide salt is used as a catalyst in an amount of sufficient to catalyze the reaction, generally 1 to 100 mol %, preferably 5 to 50 mol %, relative to the moles of compounds of Formula 2-2. And then, the quaternary organic phosphonium salt used as a catalyst can be easily recovered from the reaction mixture, as the reaction product is distilled under reduced pressure, the catalyst remains. The catalyst could be recovered to a level of 80% of the amount of catalyst initially used, and the recovered catalyst may be recrystallized from a suitable solvent, and thus reused.

The process of synthesizing the compounds represented by Formula 3-2 is performed by reacting the halomethyl arene compounds of Formula 2-2 and the arene compounds of Formula 1, using a tertiary organic phosphine or quaternary organic phosphonium salt as a catalyst. In this case, it is preferred to mix the halomethyl arene compounds of Formula 2-2 and the arene compounds of Formula 1 at a molar ratio of 4:1 to 1:3.

Meanwhile, the amount of the tertiary organic phosphine or quaternary organic phosphonium salt catalyst represented by Formula 4 or 5 or Formula 6, respectively, used as the catalyst is preferably 5 to 20 mol % relative to the compounds of Formula 2-2. As the reaction solvent in this process, depending on the reactant, for example, a reaction solvent such as an aliphatic hydrocarbon may be used, or a solvent such as ether, dimethoxyethane (DME) or THF also may be used.

When the reaction solvent as described above is used, the reactant may be uniformly distributed, and particularly when THF is used, the ring of THF is opened by the byproduct HX, to give halobutyl alcohol, and then halobutyl ether is produced through the condensation reaction of this alcohol. This would be an advantage in eliminating the byproduct of HCl gas. Furthermore, no solvent may be used when the compounds of Formula 2-2 and Formula 1 are in a liquid state. When no solvent is used, there are advantages in not only reducing the cost of the solvent, but also the purification process of the product is simple. The reaction temperature is preferably 100° C. to 250° C., more preferably 150° C. to 220° C. When the compounds are reacted under these conditions for 1 hr to 48 hrs, and then the reaction is completed, a compound represented by Formula 3-2 could be obtained when hydrogen halide is discharged by opening the stopper and the product is separated by distillation or recrystallization under atmospheric pressure or reduced pressure.

According to the present invention, the product is produced and the catalyst is separated as described above, and then the catalyst and the product are separated for recycling. Even though a tertiary organic phosphine is used as a catalyst instead of a quaternary organic phosphonium salt, the catalyst reacts with an arene compound having a halomethyl group during the reaction to give a quaternary organic phosphonium salt, so that the catalyst can be separated from the reaction product without any difficulties and used again. The catalyst quaternary organic phosphonium salt can be recovered up to a recovery rate of 80% and reused, which is very economically advantageous. When the organic phosphonium salt immobilized on a silicone resin, silica, or zeolite is used as a catalyst, it is very convenient to recover and reuse the catalyst after the reaction.

The halomethyl arene compounds of Formula 2-2 for the reaction may include the following compounds:

9-chloromethyl anthracene, 1-chloromethyl naphthalene, 1-chloromethyl-2-methylnaphthalene, chloromethylbenzene (alpha-chlorotoluene), 4-phenylbenzyl chloride, 2-methylbenzyl chloride, benzyl chloride, 4-methylbenzyl chloride, 2,5-dimethylbenzyl chloride, 3,4-dimethylbenzyl chloride, diphenylmethyl bromide, benzyl bromide, 9-bromomethyl anthracene, 1-bromomethyl naphthalene, 4-phenylthio benzyl chloride, 4-methoxybenzyl chloride, 3-methylbenzyl chloride, ρ-(trimethoxysilyl)benzyl chloride, ((chloromethyl)phenylethyl)methyldimethoxysilane, and ((chloromethyl)phenylethyl)trimethoxysilane. All of these compounds may be either commercially produced or easily synthesized.

The compound represented by Formula 1 may include compounds which may be either commercially produced or easily synthesized, such as:

benzene, toluene, o-xylene, m-xylene, p-xylene, mesitylene, ethylbenzene, propylbenzene, n-butylbenzene, isobutylbenzene, t-butylbenzene, 1,2,4,5-tetramethylbenzene, fluorobenzene, bromobenzene, iodobenzene, anisole, thioanisole, biphenyl, fluorene, o-terphenylene, m-terphenylene, p-terphenylene, naphthalene, 1-methylnaphthalene, 1-methyl-2-methylnaphthalene, biphenyl ether, biphenyl sulfide, anthracene, 9-bromoanthracene, 9-methylanthracene, 9,10-dimethylanthracene, pyrene, 1,6-dimethylpyrene, 2,7-dimethylpyrene, 1,6-diphenylpyrene, 2,7-dibenzylpyrene, 2,7-bis(diphenylmethyl)pyrene, perylene, dimethylperylene, tetracene, and pentacene.

Since the halomethyl arene compounds of Formula 2-2 could be substituted with as many as the number of hydrogens bonded to the benzene ring of the arene compound of Formula 1, various forms of products may be obtained depending on the reaction molar proportion. When the halomethyl arene compounds of Formula 2-2 are used in excess, that is, when the compounds of Formula 2-2 and the compounds of Formula 1 are reacted at a molar ratio of 4:1, a number of arylmethyl group in the arene compounds of Formula 1 could be substituted, and when the arene compounds of Formula 1 are used in excess relative to moles of the halomethyl arene compounds, that is, when the compounds of Formula 2-2 and the compounds of Formula 1 are reacted at a molar ratio of 1:3, a compound in which arylmethyl group is substituted may be obtained as a main product. The tertiary organic phosphine used as a catalyst in such a process may react with a halomethyl arene compound in the reaction process to become a quaternary organic phosphine chloride salt. The quaternary organic phosphonium salt used as a catalyst corresponds to a salt having excellent activity and has different physical properties from the reactants or products, so that the quaternary organic phosphonium salt can be easily separated and reused. For the reaction, no solvent may be separately added, and a hydrocarbon or dimethoxyethane (DME) and THF may be selectively used as a reaction solvent. When the reaction is completed, a compound represented by Formula 3-2 may be obtained by distillation or recrystallization under atmospheric pressure or reduced pressure. Hereinafter, examples will be described, in which specific methods and conditions for producing Formula 3-2 according to the present invention are described.

Example 2

Example 2-1: Synthesis of 1-benzyl naphthalene 60 g (0.47 mol) of naphthalene, 30.4 g (0.24 mol) of benzyl chloride, 4.7 g (0.024 mol) of tetrabutylphosphonium chloride, relative to 10 mol % of the number of moles of the benzyl chloride, and 100 ml of THF were placed into the high pressure reaction vessel made of a stainless steel tube having a volume of 290 ml under inert atmosphere, and the reaction mixture was reacted at 200° C. for 4 hours. This solution was taken out into a round bottom flask and distilled under reduced pressure to obtain 23.6 g (0.14 mol, yield 60%) of 1-benzyl naphthalene. As a result of 300 MHz $^1$H NMR analysis of the obtained product, Ph-CH$_2$-Ph and Ph-H were confirmed at 4.0 ppm (s, 2H) and 7.2 to 7.3 ppm (m, 5H), respectively.

Example 2-2: Synthesis of diphenylmethane 50 g (0.64 mol) of benzene, 81 g (0.64 mol) of 1-(chloromethyl)benzene, and 8.3 g (0.06 mol) of dimethylphenylphosphine were reacted at 200° C. for 3 hours in the same manner as in Example 2-1 to obtain 59.2 g (0.35 mol, yield 55%) of diphenylmethane. As a result of 300 MHz hydrogen nuclear magnetic resonance analysis of the obtained product, Ph-CH$_2$-Ph and Ph-H were confirmed at 3.8 ppm (s, 2H) and 7.0 to 7.1 ppm (m, 10H), respectively.

Example 2-3: Synthesis of 1-benzyl-4-methoxybenzene 80 g (0.74 mol) of anisole, 93.7 g (0.74 mol) of benzyl chloride, and 20.7 g (0.07 mol) of tetrabutylphosphonium chloride were reacted at 200° C. for 5 hours in the same manner as in Example 2-1 to obtain 79.3 g (0.48 mol, yield 64.3%) of 1-benzyl-4-methoxybenzene. As a result of 300 MHz hydrogen nuclear magnetic resonance analysis of the obtained product, C—OCH$_3$, Ph-CH$_2$-Ph, and a Ph-H peak were confirmed at 3.8 ppm (s, 3H), 4.1 ppm (s, 2H), and 6.9 to 7.3 ppm (m, 9H), respectively.

Example 2-4: Synthesis of 4-benzyl-1,1'-biphenyl 50 g (0.32 mol) of 1,1'-biphenyl, 54.7 g (0.32 mol) of (bromomethyl)benzene, 6.1 g (0.03 mol) of tributylphosphine, and 100 ml of THF were reacted at 200° C. for 5 hours to obtain 38.8 g (0.16 mol, yield 49.7%) of 4-benzyl-1,1'-biphenyl. As a result of 300 MHz hydrogen nuclear magnetic resonance analysis of the obtained product, Ph-CH$_2$-Ph and Ph-H were confirmed at 4.1 ppm (s, 2H) and 7.2 to 7.8 ppm (m, 14H), respectively.

Example 2-5: Synthesis of di(naphthalenyl)methane 50 g (0.39 mol) of naphthalene, 68.9 g (0.39 mol) of 1-(chloromethyl)naphthalene, 4.7 g (0.04 mol) of triethylphosphine, and 100 ml of THF were reacted at 200° C. for 5 hours in the same manner as in Example 2-1 to obtain 74.3 g (0.28 mol, yield 71%) of di(naphthalenyl)methane. As a result of 300 MHz hydrogen nuclear magnetic resonance analysis of the obtained product, Ph-CH$_2$-Ph and Naph-H were confirmed at 4.7 ppm (s, 2H) and 7.1 to 7.8 ppm (m, 14H), respectively.

Example 2-6: Synthesis of 1-benzhydrylnaphthalene 30 g (0.23 mol) of naphthalene, 56.8 g (0.23 mol) of diphenylmethyl bromide, 4.5 g (0.023 mol) of tetrabutylphosphonium chloride, and 60 ml of THF were reacted at 200° C. for 4 hours in the same manner as in Example 2-1 to obtain 35.3 g (0.12 mol, yield 50%) of 1-benzhydrylnaphthalene. As a result of 300 MHz hydrogen nuclear magnetic resonance analysis of the obtained product, Ph-CH-Ph and Ph-H were confirmed at 5.5 ppm (s, 1H) and 6.9 to 8.1 ppm (m, 17H), respectively.

Example 2-7: Synthesis of 1,5-dibenzhydrylnaphthalene 20 g (0.16 mol) of naphthalene, 97.3 g (0.48 mol) of diphenylmethyl chloride, 4.9 g (0.024 mol) of tributylphosphine corresponding to 5% of the diphenylmethyl chloride, and 60 ml of THF were reacted at 200° C. for 5 hours in the same manner as in Example 2-1 to obtain 36.8 g (0.08 mol, yield 49.4%) of 1,5-dibenzhydrylnaphthalene. As a result of 300 MHz hydrogen nuclear magnetic resonance analysis of the obtained product, C—CH—C, Ph-H. and a Naph-H peak were confirmed at 5.5 ppm (s, 2H), 7.1 to 7.3 ppm (m, 20H), and 7.0 to 8.0 (m, 6H), respectively.

Example 2-8: Synthesis of ((4-methoxyphenyl)methylene)dibenzene 50 g (0.46 mol) of anisole, 93.2 g (0.46 mol) of diphenylmethyl chloride, 14.8 g (0.05 mol) of tetrabutylphosphonium chloride, and 100 ml of THF were reacted at 200° C. for 4 hours in the same manner as in Example 2-1 to obtain 66.9 g (0.24 mol, yield 53%) of ((4-methoxyphenyl)methylene)dibenzene. As a result of 300 MHz hydrogen nuclear magnetic resonance analysis of the obtained product, O—CH$_3$, Ph-CH-Ph, and Ph-H were confirmed at 3.7 ppm (s, 3H), 5.3 ppm (s, 1H), and 6.6 to 7.1 ppm (m, 14H), respectively.

Example 2-9: Synthesis of 9-benzylanthracene 50 g (0.28 mol) of anthracene, 35.4 g (0.28 mol) of (chloromethyl)benzene, 6.1 g (0.03 mol) of tributylphosphine, and 100 ml of THF were reacted at 200° C. for 4 hours in the same manner as in Example 2-1 to obtain 37.6 g (0.14 mol, yield 50%) of 9-benzylanthracene. As a result of 300 MHz hydrogen nuclear magnetic resonance analysis of the obtained product, Ph-CH$_2$-Ph, Ph-H, and Anth-H were confirmed at 4.3 ppm (s, 2H), 7.0 to 7.2 ppm (m, 5H), and 7.3 to 7.7 ppm (m, 9H), respectively.

Example 2-10: Synthesis of 1-((2-methyl-5-naphthalenyl)methyl)naphthalene 50 g (0.35 mol) of 2-methylnaphthalene, 61.8 g (0.35 mol) of (chloromethyl)naphthalene, 11.8 g (0.04 mol) of tetrabutylphosphonium chloride, and 100 ml of THF were reacted at 200° C. for 4 hours in the same manner as in Example 2-1 to obtain 78.1 g (0.28 mol, yield 79%) of 1-((2-methyl-5-naphthalenyl)methyl)naphthalene. As a result of 300 MHz hydrogen nuclear magnetic resonance analysis of the obtained product, Ph-CH$_3$, Ph-CH$_2$-Ph, and Naph-H were confirmed at 2.5 ppm (s, 3H), 4.7 ppm (s, 2H), and 7.1 to 7.7 ppm (m, 13H), respectively.

Example 2-11: Synthesis of 9-triphenylmethylanthracene 50 g (0.28 mol) of anthracene, 78.1 g (0.28 mol) of trityl chloride, 6.1 g (0.03 mol) of tetrabutylphosphonium chloride, and 80 ml of THF were placed into a high temperature and high pressure reaction vessel made of a stainless steel tube having a volume of 290 ml under inert atmosphere, and the reaction mixture was reacted at 200° C. for 5 hours. This solution was taken out into a round bottom flask, filtered, and then distilled under reduced pressure to remove THF. THF was removed using methylene chloride, and the remaining solid was dissolved, and then treated with water to remove the catalyst. Methyl chloride was removed by distillation under reduced pressure, and recrystallization was performed by adding toluene thereto to obtain 75.7 g (0.18 mol, yield 64.3%) of 9-triphenylmethylanthracene. As a result of 300 MHz hydrogen nuclear magnetic resonance analysis of the obtained product, Ph-H and an Anth-H peak were confirmed at 7.2 ppm (m, 15H) and 7.5 and 8.3 ppm (m, 9H), respectively.

Example 2-12: Synthesis of 1-triphenylmethyl naphthalene 30 g (0.23 mol) of naphthalene, 64.1 g (0.23 mol) of triphenylmethyl chloride, 4.5 g (0.023 mol) of tetrabutylphosphonium chloride, and 60 ml of THF were reacted at 200° C. for 4 hours in the same manner as in Example 2-11 to obtain 48.2 g (0.13 mol, yield 55%) of 1-triphenylmethyl naphthalene. As a result of 300 MHz hydrogen nuclear magnetic resonance analysis of the obtained product, Ph-H and Naph-H were confirmed at 6.9 to 8.1 ppm (m, 22H).

Example 2-13: Synthesis of 9-benzhydrylanthracene 50 g (0.28 mol) of anthracene, 69.2 g (0.28 mol) of diphenylmethyl bromide, 8.9 g (0.03 mol) of tetrabutylphosphonium chloride, and 100 ml of THF were reacted at 200° C. for 4 hours in the same manner as in Example 2-11 to obtain 48.2 g (0.14 mol, yield 50%) of 9-benzhydrylanthracene. As a result of 300 MHz hydrogen nuclear magnetic resonance analysis of the obtained product, Ph-CH-Ph, Ph-H and Anth-H were confirmed at 5.3 ppm (s, 1H), 7.0 to 7.1 ppm (m, 10H), and 7.3 to 7.7 ppm (m, 9H).

Example 2-14: Synthesis of 9,10-dibenzhydrylanthracene 20 g (0.11 mol) of anthracene, 66.9 g (0.33 mol) of benzhydryl chloride, 6.5 g (0.022 mol) of tetrabutylphosphonium chloride, and 40 ml of THF were reacted at 200° C. for 5 hours in the same manner as in Example 2-11 to obtain 30.6 g of 9,10-dibenzhydryl anthracene (0.06 mol, yield 54.5%). As a result of 300 MHz hydrogen nuclear magnetic resonance analysis of the obtained product, C—CH—C, Ph-H. and an Anth-H peak were confirmed at 5.5 ppm (s, 2H), 7.0 to 7.3 ppm (m, 20H), and 7.5 to 8.2 ppm (m, 8H), respectively.

Example 2-15: Synthesis of di(9-anthracenyl)methane 30 g (0.17 mol) of anthracene, 38.5 g (0.17 mol) of chloromethyl anthracene, 5.6 g (0.02 mol) of tricyclohexylphosphine, and 60 ml of THF were reacted at 200° C. for 4 hours in the same manner as in Example 2-11 to obtain 33.2 g (0.09 mol, yield 50%) of di(9-anthracenyl)methane. As a result of 300 MHz hydrogen nuclear magnetic resonance analysis of the obtained product, Ph-CH$_2$-Ph and Anth-H were confirmed at 4.7 ppm (s, 2H) and 7.3 to 7.7 pm (m, 18H), respectively.

Example 2-16: Synthesis of 9-(4-phenylbenzyl)anthracene 50 g (0.28 mol) of anthracene, 56.8 g (0.28 mol) of 4-chloromethyl-1,1'-biphenyl, 8.9 g (0.03 mol) of tetrabutylphosphonium chloride, and 100 ml of THF were reacted at 200° C. for 5 hours in the same manner as in Example 2-11 to obtain 58.6 g (0.17 mol, yield 60%) of 9-(4-phenylbenzyl)anthracene. As a result of 300 MHz hydrogen nuclear magnetic resonance analysis of the obtained product, Ph-CH$_2$-Ph, Ph-H. and anth-H were confirmed at 4.3 ppm (s, 2H), 7.0 to 7.5 ppm (m, 9H), and 7.3 to 7.7 ppm (m, 9H), respectively.

Example 2-17: Synthesis of 4-benzhydryl-1,1'-biphenyl 50 g (0.32 mol) of 1,1'-biphenyl, 64.9 g (0.32 mol) of diphenylmethyl chloride, 5.1 g (0.03 mol) of tetramethylphosphonium bromide, and 100 ml of THF were reacted at 200° C. for 5 hours in the same manner as in Example 2-11 to obtain 49.2 g (0.15 mol, yield 48%) of 4-benzhydryl-1,1'-biphenyl. As a result of 300 MHz hydrogen nuclear magnetic resonance analysis of the obtained product, Ph-CH-Ph and Ph-H were confirmed at 5.3 ppm (s, 1H) and 7.0 to 7.5 ppm (m, 19H), respectively.

Example 2-18: Synthesis of 4-benzyl-9-anthracene 50 g (0.26 mol) of anthrone, 32.9 g (0.26 mol) of (chloromethyl)benzene, 8.9 g (0.03 mol) of tetrabutylphosphonium chloride, and 100 ml of THF were reacted at 200° C. for 4 hours in the same manner as in Example 2-11 to obtain 38.4 g (0.14 mol, yield 52%) of 4-benzyl-9-anthracenone. As a result of 300 MHz hydrogen nuclear magnetic resonance analysis of the obtained product, Ph-CH$_2$-Ph and Ph-H were confirmed at 4.1 to 4.4 ppm (d, 4H) and 7.0 to 7.6 ppm (m, 12H), respectively.

Example 2-19: Synthesis of 1-benzylpyrene 50 g (0.25 mol) of pyrene, 31.6 g (0.25 mol) of (chloromethyl)benzene, 8.9 g (0.03 mol) of tetrabutylphosphonium chloride, and 100 ml of THF were reacted at 200° C. for 4 hours in the same manner as in Example 2-11 to obtain 51.9 g (0.18 mol, yield 71%) of 1-benzylpyrene. As a result of 300 MHz hydrogen nuclear magnetic resonance analysis of the obtained product, Ph-CH$_2$-Ph, Ph-H. and Pyrene-H were confirmed at 4.3 ppm (s, 2H), 7.0 to 7.1 ppm (m, 5H), and 7.6 to 8.1 ppm (m, 9H), respectively.

Example 2-20: Synthesis of 10-((1-naphthalenyl)methyl)anthracene 50 g (0.28 mol) of anthracene, 50.0 g (0.28 mol) of 1-(chloromethyl)naphthalene, 8.9 g (0.03 mol) of tetrabutylphosphonium chloride, and 100 ml of THF were reacted at 200° C. for 4 hours in the same manner as in Example 2-11 to obtain 52.9 g (0.17 mol, yield 59%) of 10-((1-naphthalenyl)methyl)anthracene. As a result of 300 MHz hydrogen nuclear magnetic resonance analysis of the obtained product, Ph-CH$_2$-Ph. Naph-H, and Anth-H were confirmed at 4.7 ppm (s, 2H), 7.1 to 7.8 ppm (m, 7H), and 7.1 to 7.8 ppm (m, 9H), respectively.

Example 2-21: Synthesis of 6-benzylpentacene 50 g (0.18 mol) of pentacene, 61.4 g (0.36 mol) of 1-(bromomethyl)benzene, 10.6 g (0.036 mol) of tetrabutylphosphonium chloride, and 100 ml of THF were reacted at 200° C. for 3 hours in the same manner as in Example 2-11 to obtain 36.4 g (0.1 mol, yield 55%) of 6-benzylpentacene. As a result of 300 MHz hydrogen nuclear magnetic resonance analysis of the obtained product, Ph-CH$_2$-Ph, and Ph-H and Pentacene-H were confirmed at 4.3 ppm (s, 2H) and 7.0 to 7.7 ppm (m, 18H), respectively.

Example 2-22: Synthesis of 5-benzyltetracene 50 g (0.22 mol) of tetracene, 75 g (0.44 mol) of 1-(bromomethyl)benzene, 12.9 g (0.043 mol) of tetrabutylphosphonium chloride, and 100 ml of THF were reacted at 200° C. for 3 hours in the same manner as in Example 2-11 to obtain 37 g (0.1 mol, yield 53%) of 5-benzyltetracene. As a result of 300 MHz hydrogen nuclear magnetic resonance analysis of the obtained product, Ph-CH$_2$-Ph. and Ph-H and Tetracene-H were confirmed at 4.3 ppm (s, 2H) and 7.0 to 7.7 ppm (m, 16H), respectively.

Example 2-23: Synthesis of 2-benzylperylene 50 g (0.2 mol) of perylene, 86.4 g (0.4 mol) of 1-(iodomethyl)benzene, 11.7 g (0.04 mol) of tetrabutylphosphonium chloride, and 100 ml of THF were reacted at 200° C. for 3 hours in the same manner as in Example 2-11 to obtain 27.8 g (0.08 mol, yield 41%) of 2-benzylperylene. As a result of 300 MHz hydrogen nuclear magnetic resonance analysis of the obtained product, Ph-CH$_2$-Ph. and Ph-H and perylene-H were confirmed at 3.9 ppm (s, 2H) and 7.0 to 9.0 ppm (m, 16H), respectively.

Example 2-24: Synthesis of (4-(9-anthracenylmethyl)phenyl)trimethoxysilane 50 g (0.28 mol) of anthracene, 69.1 g (0.28 mol) of ((4-chloromethyl)phenyl)trimethoxysilane, 6 g (0.03 mol) of dimethylphenylphosphine, and 100 ml of n-decane were placed into a high temperature and high pressure reaction vessel made of a stainless steel tube having a volume of 290 ml under inert atmosphere, and the reaction mixture was reacted at 200° C. for 3 hours. This solution was taken out into a round bottom flask, filtered, and then distilled under reduced pressure to obtain 69.9 g (0.18 mol, yield 64.3%) of (4-(9-anthracenylmethyl)phenyl)trimethoxysilane. As a result of 300 MHz hydrogen nuclear magnetic resonance analysis of the obtained product, 0-CH$_3$, Ph-CH$_2$-Ph, Ph-H. and Anth-H were confirmed at 3.5 ppm (s, 9H), 4.3 ppm (s, 2H), 7.1 to 7.2 ppm (m, 4H), and 7.3 to 7.7 ppm (m, 9H), respectively.

Example 2-25: Synthesis of trimethoxy(4-(5-naphthalenyl)methyl)phenyl)silane 50 g (0.39 mol) of naphthalene, 96.2 g (0.39 mol) of (4-(chloromethyl)phenyl)trimethoxysilane, 4.7 g (0.04 mol) of tri ethyl phosphine, and 100 ml of n-decane were reacted at 200° C. for 4 hours in the same manner as in Example 2-24 to obtain 93.7 g (0.28 mol, yield 71%) of trimethoxy (4-(5-naphthalenyl)methyl)phenyl)silane. As a result of 300 MHz hydrogen nuclear magnetic resonance analysis of the obtained product, O—CH$_3$, Ph-CH$_2$-Ph, Ph-H, and Naph-H were confirmed at 3.6 ppm (s, 9H), 4.3 ppm (s, 2H), 7.1 ppm (m, 4H), and 7.1 to 7.8 ppm (m, 7H), respectively.

The present invention relates to processes for preparing the alkyl arene compounds represented by Formula 3-3 by the Friedel-Crafts alkylation reaction which comprises dehydrohalogenation by taking a halogen from an alkyl halide compounds of Formula 2-3 and a hydrogen from arene compounds of Formula R using a tertiary organic phosphine of Formula 4 or a quaternary organic phosphonium salt of Formula 5 or 6 as a catalyst, as illustrated by Reaction Scheme 3 below.

$$[(R^8)_y\text{---}CH_{3-y}]_m\text{---}Ar\text{---}(R^1)_z \quad \text{Formula 3-3}$$

In Formula 3-3, $R^8$=an alkyl group having 1 to 10 carbon atoms or $(CH_2)_qSi(R^\alpha)_p(OR^\beta)_{3-p}$ (q=1 to 10, $R^\alpha$=Cl or CH$_3$, p=0, 1, 2, 3, $R^\beta$=CH$_3$ or C$_2$H$_5$); y=0, 1, 2, or 3; m=1, 2, or 3; Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; $R^1$=F, Cl, Br, I, an alkyl group or phenyl group including an alkyl group or phenyl group having 1 to 8 carbon atoms; a diphenyl methyl group, and when z=0, 1, 2, 3, 4, or 5 and z≠0, each $R^1$ may have the same or different structure.

Reaction Scheme 3

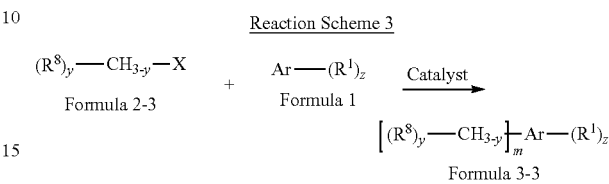

In Reaction Scheme 3, $R^8$=an alkyl group having 1 to 10 carbon atoms or $(CH_2)_qSi(R^\alpha)_p(OR^\beta)_{3-p}$ (q=1 to 10, $R^\alpha$=Cl or CH$_3$, p=0, 1, 2, 3, $R^\beta$=CH$_3$ or C$_2$H$_5$); y=0, 1, 2, or 3; X=Cl, Br, or I; Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, pentacene, or an arene compound having 1 to 8 rings; m=1, 2, or 3; $R^1$=F, Cl, Br, I, an alkyl group or phenyl group including an alkyl group or phenyl group having 1 to 8 carbon atoms; a diphenyl methyl group, and when z=0, 1, 2, 3, 4, or 5 and z≠0, each $R^1$ may have the same or different structure.

All the compounds of Formulae 4, 5 and 6 are the same as the compounds described in Reaction Scheme 1 above.

Meanwhile, in the preparing of alkyl arene compounds, the boiling point of the alkyl halide compounds of Formula 2-3 or the arene compounds of Formula 1, or the used solvent is lower than the reaction temperature of 250° C., so that the reaction needs to be performed under high pressure using a reaction vessel capable of withstanding pressure. After the alkyl halide compounds of Formula 2-3 and the arene compounds of Formula 1 are prepared, the tertiary organic phosphine or the quaternary organic phosphonium salt used as the catalyst is added in a range of 5 to 20 mol % relative to moles of the compounds of Formula 2-3 and mixed with the compounds. Thereafter, when the reaction mixture is heated to 100° C. to 250° C., preferably 150° C. to 220° C., an alkyl arene compounds such as Formula 3-3 of Reaction Scheme 3 could be synthesized. In this case, the tertiary organic phosphine used as a catalyst in the present invention reacts with an alkyl halide compounds during the reaction to become a quaternary organic phosphine halide salt. Further, the quaternary organic phosphonium salt used as a catalyst can be easily recovered from the reaction mixture, and for example, when the reaction product is distilled under reduced pressure after the reaction is completed, the catalyst remains without being distilled, and thus can be conveniently recovered. The catalyst may be recovered to a level of 80% of the amount of catalyst initially used, and the recovered catalyst may be recrystallized with a suitable solvent, and thus reused.

The synthesis process according to the present invention is performed by reacting the alkyl halide compounds of Formula 2-3 and the arene compounds of Formula 1 using a tertiary organic phosphine or quaternary organic phosphonium salt as a catalyst. In this case, it is preferred to mix the alkyl halide compounds of Formula 2-3 and the arene compounds of Formula 1 at a molar ratio of 6:1 to 1:3. When various moles of alkyl groups are substituted into the arene compounds, the reaction is performed by increasing the proportion of the alkyl halide compounds of Formula 2-3 relative to the amount of Formula 1.

Meanwhile, the amount of the tertiary organic phosphine or quaternary organic phosphonium salt catalyst represented by Formula 4 or Formula 5 or 6, respectively is used preferably 5 to 50 mol % relative to the moles of Formula 2-3. As the reaction solvent in this process, depending on the reactant, such as an aliphatic hydrocarbon may be used, or a solvent such as ether, dimethoxyethane (DME) or THF may also be used. When the reaction solvent as described above is used, the reactant may be uniformly distributed, and particularly when THF is used, the ring of THF is opened by the byproduct HX, to give halobutyl alcohol, and then halobutyl ether is produced through the condensation reaction of this alcohol, so that the byproduct HCl gas can be removed. However, when a material of Formula 2-3 including alkoxysilane or chlorosilane is used, it is not suitable for THF to be used as a solvent because the material may be hydrolyzed by the byproduct HX to give halobutyl alcohol which will cause the hydrolysis of the alkoxysilane or chlorosilane reactants. When ether having a low boiling point is used as a solvent, the solvent is completely vaporized at a reaction temperature of 200° C., which increases the pressure in the reaction vessel to increase the risk of explosion. Further, when the compounds of Formulae 2-3 and 1 are both liquids or are commercially compatible with each other, the compounds may react without a solvent. The reaction temperature is 100° C. to 250° C., preferably 150 to 220° C. When the compounds are reacted under these conditions for 1 hr to 48 hours, and then the reaction is completed, a target material may be obtained when generated hydrogen halide is discharged by opening the stopper and the product is separated by distillation or recrystallization under normal pressure or reduced pressure. As described above, after the product, the catalyst can be separated and recycled. Even though a tertiary organic phosphine is used as a catalyst instead of a quaternary phosphonium salt, the catalyst reacts with an alkyl halide compound during the reaction to give a quaternary phosphonium salt, so that the catalyst can be separated from the product without any difficulties and used again. The catalyst quaternary organic phosphonium salt can be recovered up to a recovery rate of 80% and reused, which is very economically advantageous. When the organic phosphonium salt immobilized on a silicone resin, silica, or zeolite is used as a catalyst, it is very convenient to recover and reuse the catalyst after the reaction.

As the alkyl halide compound of Formula 2-3 for reaction, it is possible to select the compound from among methyl chloride, methyl bromide, methyl iodide, ethyl chloride, ethyl bromide, ethyl iodide, 1-chloropropane, 1-bromopropane, 1-iodopropane, 2-chloropropane, 2-bromopropane, 2-iodopropane, 1-chlorobutane,1-bromobutane, 1-iodobutane, 2-chlorobutane, 2-bromobutane, 2-iodobutane, t-butyl chloride, t-butyl bromide, t-butyl iodide, 1-chloropentane, 1-bromopentane, 1-iodopentane, 2-chloropentane, 2-bromopentane, 2-iodopentane, 1-chlorohexane, 1-bromohexane, 1-iodohexane, 2-chlorohexane, 2-bromohexane, 2-iodohexane, 3-chlorohexane, 3-bromohexane, 3-iodohexane, 1-chloroheptane, 1-bromoheptane, 1-iodoheptane, 2-chloroheptane, 2-bromoheptane, 2-iodoheptane, 1-chlorooctane, 1-bromooctane, 1-iodooctane, 1-chlorononane, 1-bromononane, 1-iodononane, 1-chlorodecane, 1-bromodecane, 1-iododecane, (chloromethyl)trichlorosilane, (chloromethyl)methyldichlorosilane, (chloromethyl)dimethylchlorosilane, (chloromethyl)trimethylsilane, (chloromethyl)trimethoxysilane, (chloromethyl)triethoxysilane, (chloromethyl)methyldimethoxysilane, (chloromethyl)methyldiethoxysilane, (chloromethyl)dimethylmethoxysilane, (chloromethyl)dimethylethoxysilane, 2-chloroethyl trichlorosilane, 2-chloroethyl trimethoxysilane, 2-chloroethyl triethoxysilane, 3-chloropropyl trichlorosilane, 3-chloropropyl trimethoxysilane, 3-chloropropyl triethoxysilane, 6-chlorohexyl trichlorosilane, 6-chlorohexyl trimethoxysilane, 6-chlorohexyl triethoxysilane, and the like. All of these compounds are commercially produced materials or compounds whose synthetic methods are known in the literature.

The compounds represented by Formula 1 are the compounds which may be commercially produced or easily synthesized, and it is possible to use one or more materials selected from among benzene, toluene, o-xylene, m-xylene, p-xylene, mesitylene, ethylbenzene, propylbenzene, n-butylbenzene, isobutylbenzene, t-butylbenzene, 1,2,4,5-tetramethylbenzene, fluorobenzene, bromobenzene, iodobenzene, anisole, thioanisole, biphenyl, fluorene, o-terphenylene, m-terphenylene, p-terphenylene, naphthalene, 1-methylnaphthalene, 2-methylnaphthalene, 1-methyl-2-methylnaphthalene, biphenyl ether, biphenyl sulfide, anthracene, 9-bromoanthracene, 9-methylanthracene, 9,10-dimethylanthracene, anthrone, pyrene, 1,6-dimethylpyrene, 2,7-dimethylpyrene, 1,6-diphenylpyrene, 2,7-dibenzylpyrene, 2,7-bis(diphenylmethyl)pyrene, perylene, dimethylperylene, tetracene, and pentacene.

Since the alkyl halide compounds of Formula 2-3 may be substituted with as many as the number of hydrogens bonded to the benzene ring of the arene compound of Formula 1, various isomers of products may be obtained depending on the reaction molar proportion applied. When the alkyl halide compound of Formula 2-3 is used in excess, for example, when the compounds of Formula 2-3 and the compounds of Formula 1 are reacted at a molar ratio of 6:1, a number of alkyl substituted isomers in the arene compounds of Formula 1 may be obtained. When the arene compounds of Formula 1 are used in excess relative to the alkyl halide compounds, one alkyl substituted may be obtained as a main product. Hereinafter, examples will be described, in which specific methods and conditions for producing Formula 3-3 according to the present invention are described.

The following examples will describe the present invention in more detail, but the scope of the present invention is not limited by these examples.

Example 3

Example 3-1: Synthesis of 1-isopropyl-2-methylnaphthalene 50 g (0.35 mol) of 1-methylnaphthalene, 13.8 g (0.18 mol) of 2-chloropropane, 2.5 g (0.018 mol) of dimethylphenylphosphine, 10 mol % of the number of moles of the 2-chloropropane, and 50 ml of THF were put into a high temperature and high pressure reaction vessel made of a stainless steel tube having a volume of 290 ml under inert atmosphere, and the reaction mixture was reacted at 230° C. for 6 hours. This solution was taken out into a round bottom flask and distilled under reduced pressure to obtain 18.2 g (0.10 mol, yield 55%) of a product. As a result of 300 MHz hydrogen nuclear magnetic resonance analysis of the obtained product, C—CH$_3$, C—H$_3$. C—CH, and Naph-H were confirmed at 1.31 ppm (d, 6H), 2.62 ppm (s, 3H), 2.88 ppm (s, 1H), and 6.9 to 7.9 ppm (m, 6H), respectively.

Example 3-2: Synthesis of 1-butylnaphthalene 50 g (0.39 mol) of naphthalene, 26.7 g (0.20 mol) of 1-bromobutane, 3.9 g (0.02 mol) of tributylphosphine, and 50 ml of THF were reacted at 230° C. for 6 hours in the same manner as in Example 3-1 to obtain 17.3 g (0.09 mol, yield 47%) of a product. As a result of 300 MHz hydrogen nuclear magnetic resonance analysis of the obtained product, C—CH$_3$, C—CH$_2$—C, Naph-C—CH$_2$, Naph-CH$_2$, and Naph-CH$_2$ were confirmed at 0.89 ppm (t, 3H), 1.30 ppm (m, 2H), 1.55 ppm (m, 2H), 3.07 ppm (t, 2H), and 6.98 to 8.08 ppm (m, 7H), respectively.

Example 3-3: Synthesis of 9-(t-butyl)-10-methylanthracene 50 g (0.26 mol) of 9-methylanthracene, 12 g (0.13 mol) of t-butyl chloride, 3.6 g (0.013 mol) of tricyclohexylphosphine, and 50 ml of THF were reacted at 230° C. for 6 hours in the same manner as in Example 3-1 to obtain 18.1 g (0.07 mol, yield 56%) of a product. As a result of 300 MHz hydrogen nuclear magnetic resonance analysis of the obtained product, Anth-C—CH$_3$, Anth-CH$_3$, and Anth-H were confirmed at 1.48 ppm (s, 9H), 2.72 ppm (s, 3H), and 7.40 to 8.20 ppm (m, 8H), respectively.

Example 1-4: Synthesis of 1,5-bis(isobutyl)naphthalene 30 g (0.23 mol) of naphthalene, 55.2 g (0.7 mol) of isobutyl chloride, 8.9 g (0.03 mol) of tetrabutylphosphonium chloride, and 50 ml of THF were reacted at 230° C. for 6 hours in the same manner as in Example 3-1 to obtain 28.3 g (0.13 mol, yield 58%) of a product. As a result of 300 MHz hydrogen nuclear magnetic resonance analysis of the obtained product, C—CH$_3$, Naph-CH, and Naph-H were confirmed at 1.3 ppm (d, 12H), 2.9 ppm (m, 2H), and 7.0 to 7.9 ppm (m, 6H), respectively.

Example 3-5: Synthesis of ((4-hexylphenyl)phenyl)sulfide 50 g (0.268 mol) of biphenyl sulfide, 16.1 g (0.134 mol) of 1-chlorohexane, 4 g (0.0134 mol) of tetrabutylphosphonium chloride, and 50 ml of THF were reacted at 230° C. for 6 hours in the same manner as in Example 3-1 to obtain 4.2 g (0.163 mol, yield 61%) of a product. As a result of 300 MHz hydrogen nuclear magnetic resonance analysis of the obtained product, C—CH$_3$, C—CH$_2$—C, Ph-C—CH$_2$, Ph-C—CH$_2$, and Ph-H were confirmed at 0.88 ppm (t, 3H), 1.31 ppm (m, 6H), 1.58 ppm (m, 2H), 2.64 ppm (t, 2H), and 7.00 to 7.52 ppm (m, 9H), respectively.

Example 3-6: Synthesis of 4-(2-hexyl)-1,1'-biphenyl 50 g (0.324 mol) of biphenyl, 19.55 g (0.162 mol) of 2-chlorohexane, 3.3 g (0.0162 mol) of tributylphosphine, and 50 ml of THF were reacted at 230° C. for 6 hours in the same manner as in Example 3-1 to obtain 35.5 g (0.149 mol, yield 46%) of a product.

As a result of 300 MHz hydrogen nuclear magnetic resonance analysis of the obtained product, C—CH$_3$, Ph-C—CH$_3$, C—CH$_2$—C, Ph-C—CH$_2$, Ph-CH, and Ph-H were confirmed at 0.88 ppm (t, 3H), 1.16 ppm (d, 3H), 1.31 ppm (m, 4H), 1.54 ppm (m, 2H), 2.55 ppm (s, 1H), and 7.38 to 7.75 ppm (m, 9H), respectively.

Example 3-7: Synthesis of 6-octylpentacene 50 g (0.18 mol) of pentacene, 13.4 g (0.09 mol) of 1-bromooctane, 1 g (0.009 mol) of triethylphosphine, and 50 ml of THF were reacted at 230° C. for 6 hours in the same manner as in Example 3-1 to obtain 20.2 g (0.06 mol, yield 62%) of a product. As a result of 300 MHz hydrogen nuclear magnetic resonance analysis of the obtained product, C—CH$_3$, C—CH$_2$—C, Pentacene-C—CH$_2$, Pentacene-CH$_2$, and PentaceneH were confirmed at 0.88 ppm (t, 3H), 1.31 ppm (m, 10H), 1.61 ppm (m, 2H), 3.07 ppm (t, 2H), and 7.54 to 8.25 ppm (m, 13H), respectively.

Example 3-8: Synthesis of 1-isopropylnaphthalene 50 g (0.39 mol) of naphthalene, 15.3 g (0.195 mol) of 2-chloropropane, 5.5 g (0.0195 mol) of tricyclohexylphosphine, and 50 ml of THF were reacted at 230° C. for 6 hours in the same manner as in Example 3-1 to obtain 16.6 g (0.10 mol, yield 50%) of a product. As a result of 300 MHz hydrogen nuclear magnetic resonance analysis of the obtained product, C—CH$_3$, Naph-CH, and Naph-H were confirmed at 1.31 ppm (d, 6H), 2.28 ppm (m, 1H), and 6.98 to 8.08 ppm (m, 7H), respectively.

Example 3-9: Synthesis of 2-(t-butyl)pyrene 50 g (0.247 mol) of pyrene, 11.4 g (0.12 mol) of t-butyl chloride, 3.6 g (0.012 mol) of tetrabutylphosphonium chloride, and 50 ml of THF were reacted at 230° C. for 6 hours in the same manner as in Example 3-1 to obtain 17.4 g (0.07 mol, yield 56%) of a product. As a result of 300 MHz hydrogen nuclear magnetic resonance analysis of the obtained product, C—CH$_3$, and Pyrene-H were confirmed at 1.4 ppm (s, 9H) and 1.4 ppm (s, 9H), respectively.

Example 3-10: Synthesis of 2-sec-butylpyrene 50 g (0.247 mol) of pyrene, 22.7 g (0.124 mol) of 2-iodobutane, 3.6 g (0.0124 mol) of tetrabutylphosphonium chloride, and 50 ml of THF were reacted at 230° C. for 6 hours in the same manner as in Example 3-1 to obtain 16.3 g (0.06 mol, yield 51%) of a product. As a result of 300 MHz hydrogen nuclear magnetic resonance analysis of the obtained product, —C—CH$_3$, C—CH$_3$, C—CH$_2$—C, Pyrene-CH—C, and Pyrene-H were confirmed at 0.8 ppm (t, 3H), 1.2 ppm (d, 3H), 1.5 ppm (m, 2H), 2.6 ppm (m, 1H), and 8.0 to 8.2 ppm (m, 9H), respectively.

Example 3-11: Synthesis of 9,10-(bis(t-butyl))anthracene 30 g (0.17 mol) of anthracene, 70 g (0.51 mol) of t-butylbromide, 8.9 g (0.03 mol) of tetrabutylphosphonium chloride, and 50 ml of THF were put into a high temperature and high pressure reaction vessel made of a stainless steel tube having a volume of 290 ml, and the reaction mixture was reacted at 230° C. for 6 hours to obtain 29.6 g (0.1 mol, 62%) of a product. As a result of 300 MHz hydrogen nuclear magnetic resonance analysis of the obtained product, C—CH$_3$ and Anth-H were confirmed at 1.5 ppm (s, 18H) and 7.5 to 8.2 ppm (m, 8H), respectively.

Example 3-12: Synthesis of 1-methyl-4-(2-pentyl)benzene 50 g (0.54 mol) of toluene, 40.9 g (0.27 mol) of 2-bromopentane, and 3.7 g (0.027 mol) of dimethylphenylphosphine corresponding to 10% of the number of moles of the 2-bromopentane were put into a high temperature and high pressure reaction vessel made of a stainless steel tube having a volume of 290 ml under inert atmosphere, and the reaction mixture was reacted at 230° C. for 6 hours. This solution was taken out into a round bottom flask and distilled under reduced pressure to obtain 20.6 g (0.13 mol, yield 47%) of a product. As a result of 300 MHz hydrogen nuclear magnetic resonance analysis of the obtained product, C—CH$_3$, Ph-C—CH$_3$, C—CH$_2$—C, Ph-C—CH$_2$, Ph-CH$_3$, Ph-CH, and Ph-H were confirmed at 0.89 ppm (t, 3H), 1.16 ppm (d, 3H), 1.31 ppm (m, 2H), 1.54 ppm (m, 2H), 2.19 ppm (s, 3H), 2.55 ppm (m, 1H), and 7.06 to 7.11 ppm (m, 4H), respectively.

Example 3-13: Synthesis of 4-hexylbiphenyl 50 g (0.324 mol) of biphenyl, 19.6 g (0.162 mol) of 1-chlorohexane, 4.8 g (0.0162 mol) of tetrabutylphosphonium chloride, and 50 ml of THF were reacted at 230° C. for 6 hours in the same manner as in Example 3-12 to obtain 23.2 g ((TTO mol, yield 60%) of a product. As a result of 300 MHz hydrogen nuclear magnetic resonance analysis of the obtained product, C—CH$_3$, C—CH$_2$—C, Ph-C—CH$_2$, Ph-CH$_2$, and Ph-H were confirmed at 0.88 ppm (t, 3H), 1.30 ppm (m, 6H), 1.58 ppm (m, 2H), 2.63 ppm (t, 2H), and 7.28 to 7.75 ppm (m, 9H), respectively.

Example 3-14: Synthesis of 9-(2-hexyl)anthracene 50 g (0.28 mol) of anthracene, 16.9 g (0.14 mol) of 2-chlorohexane, 4.1 g (0.014 mol) of tetrabutylphosphonium chloride, and 50 ml of THF were reacted at 230° C. for 6 hours in the same manner as in Example 3-12 to obtain 18.4 g (0.07 mol, yield 49%) of a product. As a result of 300 MHz hydrogen nuclear magnetic resonance analysis of the obtained product, C—CH$_3$, C—CH$_2$—C and C—CH$_3$, Anth-C—CH$_2$, Anth-CH, and Anth-H were confirmed at 0.9 ppm (t, 3H), 1.3 ppm (m, 7H), 1.56 ppm (m, 2H), 2.55 ppm (m, 1H), and 7.47 to 8.24 ppm (m, 9H), respectively.

Example 3-15: Synthesis of 2-isopropyl pyrene 30 g (0.15 mol) of pyrene, 6.3 g (0.08 mol) of isopropyl chloride, 3 g (0.01 mol) of tetrabutylphosphonium chloride, and 50 ml of THF were reacted at 230° C. for 6 hours in the same manner as in Example 3-12 to obtain 12.2 g (0.05 mol, yield 59%) of a product. As a result of 300 MHz hydrogen nuclear magnetic resonance analysis of the obtained product, C—CH$_3$, Pyrene-CH, and Pyrene-H were confirmed at 1.3 ppm (d, 6H), 2.9 ppm (m, 1H), and 7.9 to 8.2 ppm (m, 9H), respectively.

Example 3-16: Synthesis of 1-sec-butyl-4-methylbenzene 50 g (0.54 mol) of toluene, 49.9 g (0.27 mol) of 2-iodobutane, 3.2 g (0.027 mol) of triethylphosphine, and 50 ml of THF were put into a high temperature and high pressure reaction vessel made of a stainless steel tube having a volume of 290 ml under inert atmosphere, and the reaction mixture was reacted at 230° C. for 6 hours. This solution was taken out into a round bottom flask and distilled under reduced pressure to obtain 21.6 g (0.15 mol, yield 54%) of a product. As a result of 300 MHz hydrogen nuclear magnetic resonance analysis of the obtained product, C—CH$_3$, Ph-C—CH$_3$, Ph-C—CH$_2$, Ph-CH$_2$, Ph-CH, and Ph-H were confirmed at 0.73 ppm (t, 3H), 1.16 ppm (d, 3H), 1.52 ppm (m, 2H), 2.19 ppm (s, 3H), 2.55 ppm (m, 1H), and 7.00 ppm (m, 4H), respectively.

Example 3-17: Synthesis of (9-(trichlorosilyl)methyl)anthracene 50 g (0.28 mol) of anthracene, 25.7 g (0.14 mol) of (chloromethyl)trichlorosilane, 1.9 g (0.014 mol) of dimethylphenylphosphine, and 50 ml of decane were put into a high temperature and high pressure reaction vessel made of a stainless steel tube having a volume of 290 ml under inert atmosphere, and the reaction mixture was reacted at 230° C. for 6 hours. This solution was taken out into a round bottom flask and washed 5 times with dried decane and filtered. This filtrate was distilled under reduced pressure to obtain 20.5 g (0.06 mol, yield 45%) of a product. As a result of 300 MHz hydrogen nuclear magnetic resonance analysis of the obtained product, Anth-CH$_2$ and Anth-H were confirmed at 3.05 ppm (s, 2H) and 7.47 to 8.20 ppm (m, 9H), respectively.

Example 3-18: Synthesis of 5-(2-(trichlorosilyl)ethyl)tetracene 50 g (0.219 mol) of tetracene, 21.7 g (0.11 mol) of 2-chloroethyl trichlorosilane, 3.2 g (0.011 mol) of tetrabutylphosphonium chloride, and 50 ml of decane were reacted at 230° C. for 6 hours in the same manner as in Example 3-17 to obtain 21.9 g (0.06 mol, yield 51%) of a product. As a result of 300 MHz hydrogen nuclear magnetic resonance analysis of the obtained product, Si—CH$_2$—C, Tetracene-CH$_2$—C, and Tetracene-H were confirmed at 1.7 ppm (t, 2H), 3.3 ppm (t, 2H) and 7.5 to 8.5 ppm (m, 11H), respectively.

Example 3-19: Synthesis of 3-(2-(trimethoxysilyl)ethyl)perylene 50 g (0.198 mol) of perylene, 18.3 g (0.099 mol) of 2-chloroethyl trimethoxysilane, 2.9 g (0.0099 mol) of tetrabutylphosphonium chloride, and 50 ml of decane were reacted at 230° C. for 6 hours in the same manner as in Example 3-17 to obtain 19.6 g (0.049 mol, yield 49%) of a product. As a result of 300 MHz hydrogen nuclear magnetic resonance analysis of the obtained product, Si—CH$_2$—C, C—CH$_2$—C, Si—OCH$_3$, and Perylene-H were confirmed at 0.93 ppm (t, 2H), 3.0 ppm (t, 2H), 3.6 ppm (s, 9H), and 7.2 to 8.2 ppm (m, 11H), respectively.

Example 3-20: Synthesis of 5-(trichloromethyl)tetracene 50 g (0.219 mol) of tetracene, 20.1 g (0.11 mol) of (chloromethyl)trichlorosilane, 1.3 g (0.011 mol) of triethylphosphine, and 50 ml of decane were reacted at 230° C. for 6 hours in the same manner as in Example 3-17 to obtain 20.7 g (0.06 mol, yield 62%) of a product. As a result of 300 MHz hydrogen nuclear magnetic resonance analysis of the obtained product, Tetracene-CH$_2$ and Tetracene-H were confirmed at 3.05 ppm (s, 2H) and 3.05 ppm (m, 11H), respectively.

Example 3-21: Synthesis of (4-phenoxybenzyl)trimethoxysilane 50 g (0.294 mol) of biphenyl ether, 25.1 g (0.147 mol) of (chloromethyl)trimethoxysilane, 4.1 g (0.0147 mol) of tricyclohexylphosphine, and 50 ml of hexane were put into a high temperature and high pressure reaction vessel made of a stainless steel tube having a volume of 290 ml under inert atmosphere, and the reaction mixture was reacted at 230° C. for 6 hours. This solution was taken out into a round bottom flask and washed 5 times with dried hexane and filtered. This filtrate was distilled under reduced pressure to obtain 20.1 g (0.07 mol, yield 45%) of a product. As a result of 300 MHz hydrogen nuclear magnetic resonance analysis of the obtained product, Si—CH$_2$, O—CH$_3$, and Ph-H were confirmed at 1.84 ppm (s, 2H), 3.55 ppm (s, 9H), and 7.06 to 7.42 ppm (m, 9H), respectively.

Example 3-22: Synthesis of 6-(trimethoxysilylmethyl)pentacene 50 g (0.18 mol) of pentacene, 15.3 g (0.09 mol) of (chloromethyl)trimethoxysilane, 1.8 g (0.009 mol) of tributylphosphine, and 50 ml of hexane were put into the reaction vessel under inert atmosphere and reacted at 230° C. for 6 hours in the same manner as in Example 3-21 to obtain 19.7 g (0.05 mol, yield 53%) of a product. As a result of 300 MHz hydrogen nuclear magnetic resonance analysis of the obtained product, Pentacen-CH$_2$, Si—OCH$_3$, and Pentacen-H were confirmed at 2.3 ppm (s, 2H), 3.6 ppm (s, 9H), and 7.5 to 8.3 ppm (m, 13H), respectively.

Example 3-23: Synthesis of 9-(2-(trichlorosilyl)ethyl)-10-methylanthracene 50 g (0.26 mol) of 9-methylanthracene, 25.7 g (0.13 mol) of 2-chloroethyl trichlorosilane, 2.6 g (0.013 mol) of tributylphosphine, and 50 ml of hexane were reacted at 230° C. for 6 hours in the same manner as in Example 3-21 to obtain 25.8 g (0.07 mol, yield 56%) of a product. As a result of 300 MHz hydrogen nuclear magnetic resonance analysis of the obtained product, Si—CH$_2$, Anth-CH$_3$, Si—C—CH$_2$, and Anth-H were confirmed at 1.7 ppm (t, 2H), 2.7 ppm (t, 3H), 3.3 ppm (t, 2H), and 7.5 to 8.2 ppm (m, 8H), respectively.

Example 3-24: Synthesis of 1-(2-(trimethoxysilyl)ethyl)naphthalene 50 g (0.39 mol) of naphthalene, 36 g (0.195 mol) of 2-chloroethyl trimethoxysilane, 5.8 g (0.0195 mol) of tetrabutylphosphonium chloride, and 50 ml of hexane were reacted at 230° C. for 6 hours in the same manner as in Example 3-21 to obtain 24.3 g (0.09 mol, yield 45%) of a product. As a result of 300 MHz hydrogen nuclear magnetic resonance analysis of the obtained product, Si—CH$_2$, Si—C—CH$_2$, Si—OCH$_3$, and Naph-H were confirmed at 0.9 ppm (t, 2H), 2.9 ppm (t, 2H), 3.6 ppm (s, 9H), and 6.9 to 8.1 ppm (m, 7H), respectively.

Example 3-25: Synthesis of 9-((trimethoxysilyl)methyl)anthracene 50 g (0.28 mol) of anthracene, 23.9 g (0.14 mol) of (chloromethyl)trimethoxysilane, 4.1 g (0.014 mol) of tetrabutylphosphonium chloride, and 50 ml of decane were reacted at 230° C. for 6 hours in the same manner as in Example 3-21 to obtain 21 g (0.07 mol, yield 48%) of a product. As a result of 300 MHz hydrogen nuclear magnetic resonance analysis of the obtained product, Si—CH$_2$, Si—OCH$_3$, and Anth-H were confirmed at 2.28 ppm (s, 2H), 3.55 ppm (s, 9H), and 7.47 to 8.28 ppm (m, 9H), respectively.

Example 3-26: Synthesis of 6-(2-(trichlorosilyl)ethyl)pentacene 50 g (0.18 mol) of pentacene, 17.8 g (0.09 mol) of 2-chloroethyl trichlorosilane, 2.7 g (0.009 mol) of tetrabutylphosphonium chloride, and 50 ml of decane were reacted at 230° C. for 6 hours in the same manner as in Example 3-21 to obtain 20.6 g (0.05 mol, yield 52%) of a product. As a result of 300 MHz hydrogen nuclear magnetic resonance analysis of the obtained product, Si—CH$_2$, Si—C—CH$_2$, and Pentacen-H were confirmed at 1.70 ppm (t, 2H), 3.30 ppm (t, 2H), and 7.54 to 8.25 ppm (m, 13H), respectively.

Example 3-27: Synthesis of 4-((trichlorosilyl)methyl)toluene 50 g (0.543 mol) of toluene, 49.9 g (0.27 mol) of (chloromethyl)trichlorosilane, and 8 g (0.027 mol) of tetrabutylphosphonium chloride were put into a high temperature and high pressure reaction vessel made of a stainless steel tube having a volume of 290 ml in a nitrogen atmosphere, and the reaction mixture was reacted at 230° C. for 6 hours to obtain 38.8 g (0.16 mol, yield 60%) of a product. As a result of 300 MHz hydrogen nuclear magnetic resonance analysis of the obtained product, Ph-CH$_3$, Si—CH$_2$, and Ph-H were confirmed at 2.19 ppm (s, 3H), 2.61 ppm (s, 2H), and 7.01 to 7.11 ppm (m, 4H), respectively.

Example 3-28: Synthesis of 1,5-bis((trichlorosilyl)methyl)naphthalene 30 g (0.23 mol) of naphthalene, 126.9 g (0.69 mol) of chloromethyl trichlorosilane, 11.8 g (0.04 mol) of tetrabutylphosphonium chloride corresponding to 5% of the number of moles of the chloromethyl trichlorosilane, and 40 ml of hexane were put into a high temperature and high pressure reaction vessel made of a stainless steel tube having a volume of 290 ml in a nitrogen atmosphere, and the reaction mixture was reacted at 230° C. for 6 hours. This solution was taken out into a round bottom flask and washed 5 times with dry hexane and filtered. This filtrate was distilled under reduced pressure to obtain 59.2 g (0.14 mol, yield 63%) of a product. As a result of 300 MHz hydrogen nuclear magnetic resonance analysis of the obtained product, Si—CH$_2$ and Naph-H were confirmed at 3.1 ppm (s, 4H) and 6.9 to 7.8 ppm (m, 6H), respectively.

Example 3-29: Synthesis of 9,10-bis((trimethoxysilyl)methyl)anthracene 20 g (0.11 mol) of anthracene, 58 g (0.34 mol) of chloromethyl trimethoxysilane, 5.9 g (0.02 mol) of tetrabutylphosphonium chloride, and 50 ml of hexane were reacted at 230° C. for 6 hours in the same manner as in Example 3-28 to obtain 26.8 g (0.06 mol, yield 57%) of a product. As a result of 300 MHz hydrogen nuclear magnetic resonance analysis of the obtained product, Si—CH$_2$, Si—OCH$_3$, and Anth-H were confirmed at 2.3 ppm (s, 4H), 3.6 ppm (s, 9H), and 7.5 to 8.2 ppm (m, 8H),

Example 3-30: Synthesis of 9,10-bis((2-dichloromethylsilyl)ethyl)anthracene 20 g (0.11 mol) of anthracene, 58.6 g (0.33 mol) of 2-chloroethylmethyldichlorosilane, 5.9 g (0.02 mol) of tetrabutylphosphonium chloride, and 50 ml of hexane were reacted at 230° C. for 6 hours in the same manner as in Example 3-28 to obtain 29.9 g (0.06 mol, yield 59%) of a product. As a result of 300 MHz hydrogen nuclear magnetic resonance analysis of the obtained product, Si—$CH_3$, Si—$CH_2$, Anth-$CH_2$, and Anth-H were confirmed at 0.7 ppm (s, 6H), 0.9 ppm (t, 4H), 2.9 ppm (t, 4H), and 7.5 to 8.2 ppm (m, 8H), respectively.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. A method for producing an alkyl arene compound represented by Formula 3-1 produced by the Friedel-Crafts alkylation reaction, the method comprising reacting a compound represented by Formula 1 with a compound represented Formula 2-1 in the presence of an organic phosphine compound as a catalyst, where:

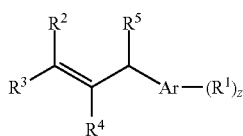

Formula 3-1

Formula 1

$Ar—(R^1)_z$ in Formula 1, Ar=benzene, naphthalene, anthracene, anthrone, biphenyl, terphenyl, anthraquinone, pyrene, perylene, biphenyl ether, biphenyl sulfide, anisole, fluorene, thioanisole, tetracene, phenanthrene, biphenyl sulfide, or pentacene; $R^1$=F, Cl, Br, I, an alkyl group or phenyl group comprising an alkyl group or phenyl group having 1 to 8 carbon atoms, or a diphenyl methyl group; and z=0, 1, 2, 3, 4, or 5 and each $R^1$ has the same or different structure

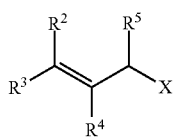

Formula 2-1 in compounds of Formula 2-1, $R^2$=H, Me, $CH_2Cl$ or $CH_2Br$; $R^3$=H, Me, Ph, $CH_2Cl$, or $CH_2Br$; $R^4$=H, Me, $CH_2Cl$, or $CH_2Br$; $R^5$=H or Me; and X=Cl, Br, or I.

2. The method of claim 1, wherein a compound represented by Formula 4 is used as the catalyst, Formula 4:

$P(R")_3$, wherein R" comprises a phenyl group, an alkyl group having 1 to 12 carbon atoms, or an alkenyl group having 2 to 12 carbon atoms, and different R"s from a cyclic structure linked by a covalent bond.

3. The method of claim 1, wherein a concentration of the catalyst is 5 to 20 mol % with respect to the compound of Formula 2-1.

4. The method of claim 1, wherein a compound represented by Formula 5 is used as the catalyst, Formula 5:

$R'P(R")_3X$, wherein R" comprises a phenyl group, an alkyl group having 1 to 12 carbon atoms, or an alkenyl group having 2 to 12 carbon atoms, and different R"s form a cyclic structure linked by a covalent bond, R' is the same as $R^{2-5}$ in Formula 2-1, and X is one selected from Cl, Br, or I.

5. The method of claim 1, wherein a concentration of the catalyst is 5 to 20 mol % with respect to the compound of Formula 2-1.

6. The method of claim 1, wherein a compound represented by Formula 6 is used as the catalyst, Formula 6:

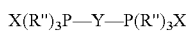

$X(R")_3P—Y—P(R")_3X$ wherein R" comprises a phenyl group, an alkyl group having 1 to 12 carbon atoms, or an alkenyl group having 1 to 12 carbon atoms, different R"s form a cyclic structure linked by a covalent bond, X is Cl, Br, or I, and Y=an alkyl group having 1 to 12 carbon atoms, an alkyl group comprising an aromatic group, or an aromatic group.

7. The method of claim 1, wherein a concentration of the catalyst is 5 to 20 mol % with respect to the compound of Formula 2-1.

8. The method of claim 1, wherein a reaction molar ratio of the compound represented by Formula 2-1 to the compound represented by Formula 1 is 6:1 to 1:3.

9. The method of claim 1, wherein a concentration of the catalyst is 5 to 20 mol % with respect to the compound of Formula 2-1.

10. The method of claim 1, wherein a reaction temperature is 100 to 250° C.

11. The method of claim 1, wherein the reaction is carried in the absence of a reaction solvent or in the presence of a reaction solvent selected from the group consisting of a hydrocarbon, ether, dimethoxyethane (DME), THF, and combinations thereof.

12. The method of claim 1, wherein a concentration of the catalyst is 5 to 20 mol % with respect to the compound of Formula 2-1.

* * * * *